(12) United States Patent
Gorski et al.

(10) Patent No.: US 8,076,308 B2
(45) Date of Patent: Dec. 13, 2011

(54) INHIBITION OF AUTOPHAGY GENES IN CANCER CHEMOTHERAPY

(75) Inventors: Sharon Margaret Gorski, Vancouver (CA); Mohammad Abdul Qadir, Vancouver (CA)

(73) Assignee: British Columbia Cancer Agency, Vancouver, British Columbia (CA)

( * ) Notice: Subject to any disclaimer, the term of this patent is extended or adjusted under 35 U.S.C. 154(b) by 29 days.

(21) Appl. No.: 12/092,780

(22) PCT Filed: Nov. 3, 2006

(86) PCT No.: PCT/CA2006/001822
§ 371 (c)(1),
(2), (4) Date: Oct. 17, 2008

(87) PCT Pub. No.: WO2007/051316
PCT Pub. Date: May 10, 2007

(65) Prior Publication Data
US 2010/0129429 A1 May 27, 2010

Related U.S. Application Data

(60) Provisional application No. 60/733,769, filed on Nov. 7, 2005.

(51) Int. Cl.
*C12N 15/11* (2006.01)
(52) U.S. Cl. .................................. 514/44 A
(58) Field of Classification Search ............... 514/44 A
See application file for complete search history.

(56) References Cited

U.S. PATENT DOCUMENTS

| 6,982,252 | B2 | 1/2006 | Paglin et al. |
| 2002/0156025 | A1 | 10/2002 | Paglin et al. |
| 2004/0259247 | A1* | 12/2004 | Tuschl et al. .................. 435/375 |

OTHER PUBLICATIONS

Ui-Tei et al. (Nucleic Acids Research, 2004, 34(3):936-948).*
Santiago, F.S. et al. New DNA enzyme targeting Egr-1 mRNA inhibits vascular smooth muscle proliferation and regrowth after injury. Nature Medicine. 1999, vol. 5, pp. 1264-1269.
Dykxhoorn, D. M., et al. The silent treatment: siRNAs as small molecule drugs. Gene Therapy. 2006, vol. 13, pp. 541-552.
Morrissey, D. V., et al. Potent and persistent in vivo anti-HBV activity of chemically modified siRNAs. Nature Biotechnology. 2005, vol. 23, No. 8, pp. 1002-1007.
Santel, A., et al. RNA interference in the mouse vascular endothelium by systemic administration of siRNA-lipoplexes for cancer therapy. Gene Therapy. 2006, vol. 13, No. 18, pp. 1360-1370.
Hubbard, T. J. P., et al. Ensembl 2007. Nucleic Acid Research. 2007, vol. 35, database issue: D610-D617.
Klionsky, D. J., et al. A unified nomenclature for yeast autophagy-related genes. Developmental Cell. 2003, vol. 5, No. 4, pp. 539-545.
Mizushima, N., et al. Autophagosome Formation in Mammalian Cells. Cell Structure and Function. 2002, v. 27, No. 6, pp. 421-429.
National Cancer Institute of Canada. Canadian Cancer Statistics 2004, Toronto, Canada, 2004.

Levine, B., Klionsky, D. J. Development by self-digestion: molecular mechanisms and biological functions of autophagy. Developmental Cell. 2004, vol. 6, No. 4, pp. 463-477.
Shintani, T., Klionsky, D. J. Autophagy in health and disease: a double-edged sword. Science. 2004, vol. 306, pp. 990-995.
Klionsky, D. J., Emr, S. D. Autophagy as a regulated pathway of cellular degradation. Science. 2000, vol. 290, pp. 1717-1721.
Sledz, C. A., et al. Activation of the interferon system by short-interfering RNAs. Nature Cell Biology. 2003, vol. 5, No. 9, pp. 834-839.
Yue Z., et al. Beclin 1, an autophagy gene essential for early embryonic development, is a haploinsufficient tumor suppressor. Proceedings of the National Academy of Sciences of the United States of America. 2003, vol. 100, No. 25, pp. 15077-15082.
Bursch, W., et al. Active cell death induced by the anti-estrogens tamoxifen and ICI 164 384 in human mammary carcinoma cells (MCF-7) in culture: the role of autophagy. Carcinogenesis. 1996, vol. 17, pp. 1595-1607.
Bilir, A., et al. Autophagy and nuclear changes in FM3A breast tumor cells after epirubicin, medroxyprogesterone and tamoxifen treatment in vitro. Pathobiology. 2001, vol. 69, No. 3, pp. 120-126.
Paglin, S., et al. A novel response of cancer cells to radiation involves autophagy and formation of acidic vesicles. Cancer Research. 2001, vol. 61, pp. 439-444.
McManus, M. T., et al. Gene silencing in mammals by small interfering RNAs. Nature Reviews Genetics. 2002, vol. 3, No. 10, pp. 737-747.
Bursch, W., et al. Autophagic and apoptotic types of programmed cell death exhibit different fates of cytoskeletal filaments. Journal of Cell Science. 2000, vol. 113, Pt. 7, pp. 1189-1198.
Boya, P., et al. Inhibition of macroautophagy triggers apoptosis. Molecular and Cellular Biology. 2005, vol. 25, pp. 1025-1040.
Mizushima, N. Methods for monitoring autophagy. International Journal of Biochemistry and Cell Biology. 2004, vol. 36, No. 12, pp. 2491-2502. Dragowska, W. H., et al. HER-2/neu overexpression increases the viable hypoxic cell population within solid tumors without causing changes in tumor vascularization. Molecular Cancer Research. 2004, vol. 2, No. 11, pp. 606-619.
Waterhouse, D. N., et al. Trastuzumab and Liposomal Doxorubicin in the Treatment of MCF-7 Xenograft Tumor-Bearing Mice: Combination does not affect drug serum levels. Pharmaceutical Research. 2005, vol. 22, No. 6, pp. 915-922.
Brummelkamp, T. R., et al. A system for stable expression of short interfering RNAs in mammalian cells. Science. 2002, vol. 296, No. 5567, pp. 550-553.
Minakuchi, Y., et al. Atelocollagen-mediated synthetic small interfering RNA delivery for effective gene silencing in vitro and in vivo. Nucleic Acids Research. 2004, vol. 32, No. 13, p. e109.
Lee, J. H., et al. Suppression of progression and metastasis of established colon tumors in mice by intravenous delivery of short interfering RNA targeting KITENIN, a metastasis-enhancing protein. Cancer Research. 2005, vol. 65, No. 19, pp. 8993-9003.
Yu, L., et al. Regulation of an ATG7-beclin 1 program of autophagic cell death by caspase-8. Science 2004, vol. 304, No. 5676, pp. 1500-1502.

(Continued)

*Primary Examiner* — Jon E Angell
(74) *Attorney, Agent, or Firm* — Bozicevic, Field & Francis LLP; Bret E. Field

(57) ABSTRACT

There is provided compositions and methods for improving the therapeutic efficacy of various cancer treatments, for example endocrine therapy, chemotherapy or radiation therapy, by inhibiting the expression of one or more genes involved in the cellular autophagy response. The compositions include compositions comprising an siRNA directed against an Atg gene and may be used to inhibit expression of an Atg gene in a cell currently undergoing cancer therapy, or to treat, inhibit or prevent cancer in a subject in combination with a cancer therapy.

7 Claims, 13 Drawing Sheets

OTHER PUBLICATIONS

Bonetta, L. RNAi: Silencing never sounded better. Nature Methods. 2004, vol. 1, No. 1, pp. 79-86.

Pushparaj, P. N., Melendez, A. J. Short interfering RNA (siRNA) as a novel therapeutic. Clinical and Experimental Pharmacology and Physiology. 2006, vol. 33, No. 5-6, pp. 504-510.

Pattingre, S., et al. Bcl-2 antiapoptotic proteins inhibit Beclin 1-dependent autophagy. Cell. 2005, vol. 122, No. 6, pp. 927-939.

Opipari, A. W., et al. Resveratrol induced autophagocytosis in ovarian cancer cells. Cancer Research. 2004, vol. 64, No. 2, pp. 696-703.

Ito, H., et al. Radiation-induced autophagy is associated with LC3 and its inhibition sensitizes malignant glioma cells. International Journal of Oncology. 2005, vol. 26, No. 5, pp. 1401-1410.

Chou, T. C., Talalay, P. Quantitative analysis of dose-effect relationships: the combined effects of multiple drugs or enzyme inhibitors. Advances in Enzyme Regulation. 1984, vol. 22, pp. 27-55.

Kondo, Y., et al. The role of autophagy in cancer development and response to therapy. Nature Reviews Cancer. 2005, vol. 5, pp. 726-734.

Wu, L., et al. Effects of the mammalian target of rapamycin inhibitor CCI-779 used alone or with chemotherapy on human prostate cancer cells and xenografts. Cancer Research. 2005, vol. 65, No. 7, pp. 2825-2831.

Qadir, A. M., et al. Sensitizing breast cancer cells to chemotherapy by inhibiting autophagy. Poster presentation Nov. 4, 2005.

Yoshimori, T., et al. Autophagy: a regulated bulk degradation process inside cells. Biochemical and Biophysical Research Communications. 2004, vol. 313, No. 2, pp. 453-458.

Niemann, A., et al. The lysosomotropic agent monodansylcadaverine also acts as a solvent polarity probe. Journal of Histochemistry and Cytochemistry. 2000, vol. 48, No. 2, pp. 251-258.

Tsujimoto, Y., Shimizu, S. Another way to die: autophagic programmed cell death. Cell Death and Differentiation. 2005, vol. 12, pp. 1528-1534.

Abedin, M. J., et al. Autophagy delays apoptotic death in breast cancer cells following DNA damage. Cell Death and Differentiation. 2006, pp. 1-11.

Hippert, M. M., et al. Autophagy in cancer: good, bad, or both? Cancer Research. 2006, vol. 66, No. 19, 9349-9351.

Boya, P., et al. Inhibition of macroautophagy triggers apoptosis. Molecular and Cellular Biology. 2005, vol. 25, No. 3, pp. 1025-1040.

Takacs-Vellai et al., "Inactivation of the Autophagy Gene bec-1 Triggers Apoptotic Cell Death in *C. elegans*" Current Biology, Current Science, GB LNKD; vol. 15, No. 16 (2005) pp. 1513-1517.

\* cited by examiner

| Gene | siRNA sequence | SEQ ID NO. |
|---|---|---|
| Beclin 1 | GCU GUU UGG AGA UCU UAG AGC AAA U | 1 |
| Beclin 1 | AUU UGC UCU AAG AUC UCC AAA CAG C | 13 |
| Scrambled Control | GCU UUG GGA UAU CAU AGC GAU GAA U | 14 |
| Scrambled Control | AUU CAU CGC UAU GAU AUC CCA AAG C | 15 |
| Beclin 1 | GGA UGA UGA GCU GAA GAG UGU UGA A | 2 |
| Beclin 1 | UUC AAC ACU CUU CAG CUC AUC AUC C | 16 |
| Scrambled Control | GGA AGU AGU CGA GAA UGU GUG UGA A | 17 |
| Atg7 | GCU GGA UGA AGC UCC CAA GGA CAU U | 6 |
| Atg7 | AAU GUC CUU GGG AGC UUC AUC CAG C | 18 |
| Atg7 | CCA AGG AUG GUG AAC CUC AGU GAA U | 7 |
| Atg7 | AUU CAC UGA GGU UCA CCA UCC UUG G | 19 |
| Atg7 | AAA CCU UUG AUC CAA ACC CAC UGG C | 8 |
| Scrambled Control | GCC GGG UGU UUC UAG GAA AGG AUU U | 21 |
| Scrambled Control | AAA UCC UUU CCU AGA AAC ACC CGG C | 20 |
| Atg5 | GAU CAC AAG CAA CUC UGG AUG GGA U | 9 |
| Atg5 | AUU CCA UGA GUU UCC GAU UGA UGG C | 10 |
| Atg5 | GCC AUC AAU CGG AAA CUC AUG GAA U | 22 |
| Atg5 | AAA CAA GUU GGA AUU CGU CCA AAC C | 11 |
| Atg5 | GGU UUG GAC GAA UUC CAA CUU GUU U | 23 |
| Atg5 | AUC CAU CCA GAG UUG CUU GUG AUC | 12 |
| Beclin 1 | UAU CUG UGC AUU CCU CAC AGA GUG G | 3 |
| Beclin 1 | CCA CUC UGU GAG GAA UGC ACA GAU A | 24 |
| Beclin 1 | AGC UGC UGU CGU UUA AAU UCA CUG U | 4 |
| Beclin 1 | ACA GUG AAU UUA AAC GAC AGC AGC U | 25 |
| Beclin 1 | UUC AAC ACU CUU CAG CUC AUC AUC C | 5 |
| Beclin 1 | GGA UGA UGA GCU GAA GAG UGU UGA A | 26 |
| Scrambled Control | GCC GGG UGU UUC UAG GAA AGG AUU U | 27 |
| Scrambled Control | AAA UCC UUU CCU AGA AAC ACC CGG C | 28 |

FIGURE 1

1
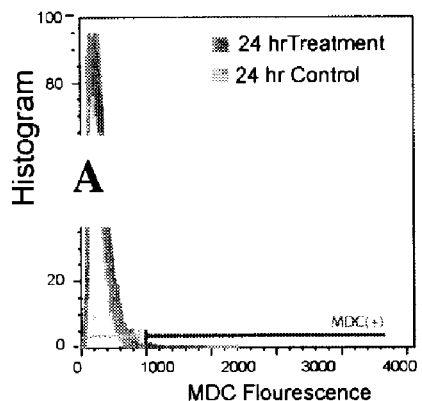
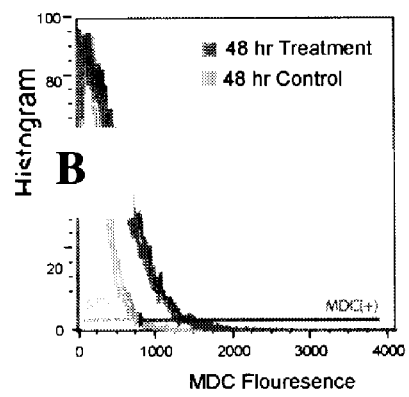
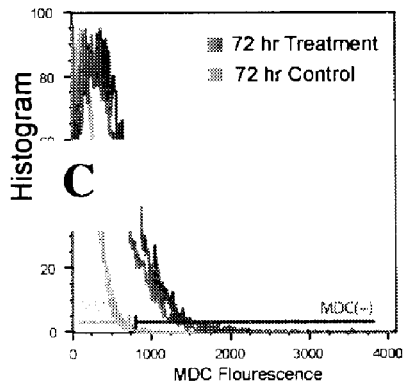
2
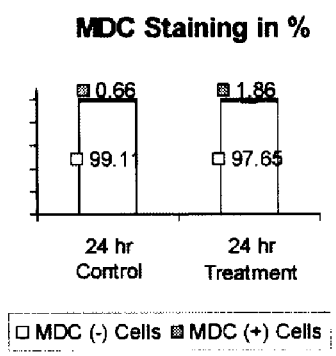
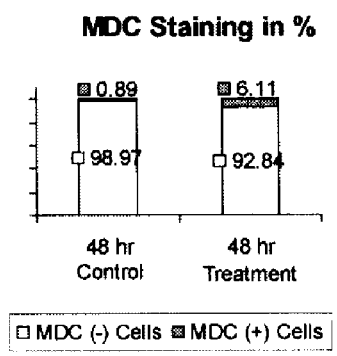
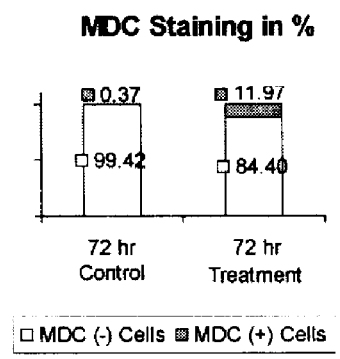
FIGURE 2

INHIBITION OF AUTOPHAGY GENES IN CANCER CHEMOTHERAPY

CROSS-REFERENCE TO RELATED APPLICATION

This application claims benefit and priority from U.S. provisional patent application No. 60/733,769 filed on Nov. 7, 2005, the contents of which are incorporated herein by reference.

FIELD OF THE INVENTION

The present invention relates generally to compositions and methods for treating cancer.

BACKGROUND OF THE INVENTION

Cancer is a major health concern and major cause of mortality worldwide. In the year 2000, malignant tumours were responsible for 12 percent of nearly 56 million deaths worldwide from all causes. In many countries, more than a quarter of all deaths are attributable to cancer. In 2000, 5.3 million men and 4.7 million women developed a malignant tumour and altogether 6.2 million died from the disease. Cancer has emerged as a major public health problem in developing countries, matching its effect in industrialized nations.

Annual new cancer cases are predicted to rise from 10 million new cases globally in 2000 to 15 million new cases globally in 2020. This prediction is based on the fact that populations are steadily aging in both developed and developing countries, as well as current trends in smoking prevalence and the growing adoption of unhealthy lifestyles.

Therefore, there exists a need for new strategies to treat and prevent cancer, including strategies that aim to improve the efficacy and therapeutic response of existing radiation, endocrine therapeutic and chemotherapeutic treatments.

SUMMARY OF THE INVENTION

This invention provides compositions and methods for improving the therapeutic efficacy of various cancer treatments, for example endocrine therapy, chemotherapy or radiation therapy, by inhibiting the cellular process of macroautophagy, also referred to commonly as autophagy.

Autophagy is thought to involve a relatively complex cascade of molecular interactions, driven by a variety of genes. Molecular cascades of the sort involved in autophagy often involve redundant and compensatory mechanisms that render these physiologically important responses recalcitrant to external modulation. It has surprisingly been demonstrated in the present Examples that the autophagy response is amenable to a sufficient degree of modulation by way of external regulation of gene expression, to provide a physiological response that is therapeutically relevant.

By inhibiting the expression of cellular genes required for the autophagic response, either causally or through regulatory associations, the therapeutic efficacy of regimens commonly employed to treat cancer, such as for example, endocrine therapy, chemotherapy or radiation therapy, is significantly improved.

In one aspect, there is provided a method of increasing a cellular response to a cancer therapy comprising inhibiting expression of an Atg gene in a cell currently undergoing the cancer therapy.

In another aspect, there is provided a method of treating, inhibiting or preventing cancer comprising administering an effective amount of an agent that is capable of inhibiting expression of an Atg gene, in combination with a cancer therapy.

In another aspect, there is provided an siRNA comprising a sequence as set forth in any one of SEQ ID NO.: 1 to SEQ ID NO.: 12.

In another aspect, there is provided a pharmaceutical composition comprising the siRNA molecule as described herein and a pharmaceutically acceptable diluent.

In particular embodiments, the invention involves application of siRNA methodology to knock-down genes involved in autophagy, including cyto-protective autophagy, particularly in a breast cancer cell treated with tamoxifen or a related taxane. siRNA technology is advantageous due to its high selectivity and reduced non-specificity, and is rapidly being adopted as a therapeutic approach which can be delivered systemically to a subject.

Further aspects of the invention will become apparent from consideration of the ensuing description of preferred embodiments of the invention. A person skilled in the art will realise that other embodiments of the invention are possible and that the details of the invention can be modified in a number of respects, all without departing from the inventive concept. Thus, the following drawings, descriptions and examples are to be regarded as illustrative in nature and not restrictive.

BRIEF DESCRIPTION OF THE DRAWINGS

In the figures, which illustrate, by way of example only, embodiments of the present invention, FIG. 1 represents the sequences of various siRNAs that inhibit expression of Atg genes Atg7 or Beclin 1 and various control siRNAs;

FIG. 2 is histograms and graphs depicting cells in MDC (−) and MDC (+) gates of MCF-7 cell populations treated with Tamoxifen and sorted by FACS;

DETAILED DESCRIPTION

Figure 3:
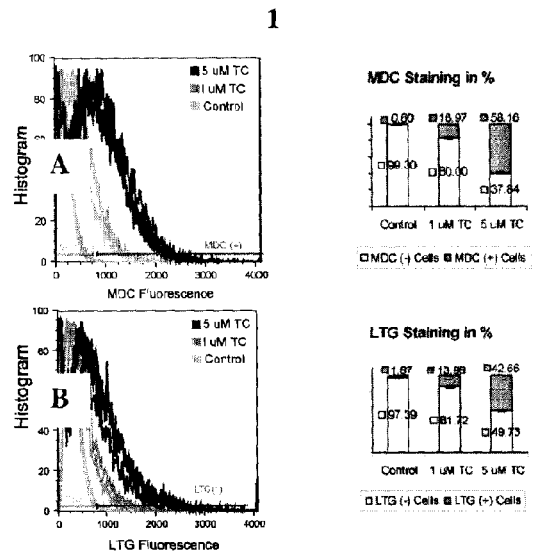
FIG. 3 is histograms and graphs depicting cells in cell populations treated with Tamoxifen and sorted by FACS analysis using the markers MDC and LysoTracker Green.

In various aspects, the compositions and methods described herein relate to inhibition of the cellular processes involved in autophagy, for example to improve the therapeutic response in a cell that is undergoing treatment for a disorder, for example in combination with a treatment for a disorder. The treatment for the disorder may be one that induces a protective autophagy response, meaning that autophagy is induced in order to prolong cell survival in response to the treatment. Alternatively, the disorder may be a disorder in which a protective autophagy response occurs. For example, the treatment may be a cancer treatment such as endocrine therapy, chemotherapy or radiation therapy, which induces treated cells to initiate or up-regulate an autophagic response in an attempt to survive the treatment.

Thus, although one aspect of the invention relates to the treatment of cancers, other aspects of the invention relate to any disorder in which autophagy is up-regulated and plays a protective role in the disorder, or in which treatment of the disorder induces autophagy in an effort by the cell to survive treatment-induced death, or in which inhibition of cyto-protective autophagy may be beneficial to treatment of the disorder.

Macroautophagy, hereinafter referred to as autophagy ("self-eating"), is a ubiquitous cellular process thought to be responsible for the routine degradation of long-lived proteins and the turnover of organelles. Autophagy reportedly also enables cell survival during nutrient starvation and recent findings suggest that it may play a role in processes as diverse as differentiation, tissue remodeling and aging (2). Autophagy is characterized by the formation of a sequestering or isolation membrane that enwraps bulk cytoplasm and organelles. Closure of the membrane results in formation of a double-membrane vesicle called an autophagosome which then fuses with a lysosome. The resulting autolysosome degrades the inner membrane of the autophagosome and its contents that can then be recycled by the cell (3).

Genes involved in autophagy were discovered primarily by genetic screens in yeast (4, 5) and are now unified under the common name of Atg (autophagy-related) (6). Many of the 18 Atg gene products discovered in yeast are evolutionarily conserved from amoebae to mammals (6). The Atg gene products function primarily in two ubiquitin-like conjugation systems required for autophagosome formation (5). The identification of Atg genes has provided markers for autophagy.

The present invention is based in part on the surprising demonstration that a cytoprotective autophagic response of cells to certain therapies, for example cancer therapies, may be counteracted by inhibiting the expression of an Atg gene. The invention accordingly provides approaches to inhibiting the expression of genes (i.e. beclin, Atg7, Atg5) involved in this protective autophagic response, either concurrent to or after therapy, for improving the efficacy of a relevant therapy, such as cancer therapy, including endocrine therapeutic, chemotherapeutic or radiation treatments.

Thus, in one aspect, methods are provided for increasing a cellular or therapeutic response to a cancer therapy. The method may comprise inhibiting expression of an Atg gene in a cell currently undergoing the cancer therapy. In this context, "cellular response" refers to the reaction of a cell that is currently being treated with a cancer therapy, including a known cancer therapy or a new cancer therapy, as a consequence of such treatment. Alternative cellular responses may for example include cell death, apoptosis, induction of DNA damage, induction of cell cycle arrest, induction of cytostasis, activation of signalling pathways including those involving p53, Bcl-2 family, caspases, cyclins, CDKs, pRb, PKC, MAPK and PI3K/Akt, increased expression of apoptotic genes, increased survival, for example due to induction of a cyto-protective autophagy response, or increased expression of autophagy genes. Cell death or apoptosis can be measured using standard apoptosis assays or by detecting known apoptotic markers, for example, cytochrome c release, loss of mitochondrial membrane potential, caspase-3 activation, caspase-9 processing, PARP cleavage or increased sub-G1 population in a cell culture or cell population, as will be understood in the art.

In the context of the invention "increasing" the cellular response refers to increasing the rate at which, or the degree to which, a cell responds to the cancer therapy, increasing or augmenting the effect of the cancer therapy on a cell, or increasing the likelihood that a cell will respond to the cancer therapy, as compared with the cellular response to the cancer therapy alone in the absence of the present methods.

In the context that the cellular response occurs in a cell that is currently being treated with a cancer therapy, the term "cell" refers to a single cell, a plurality of cells or a population of cells, unless otherwise indicated herein. The cell may be a cancerous cell, a pre-cancerous cell, a cell that is suspected of being cancerous or pre-cancerous, a cell that is pre-disposed to becoming cancerous or pre-cancerous, or a cell that is desired to be prevented from becoming cancerous or pre-cancerous. The cell may be a transformed cell or a cell undergoing, suspected of undergoing or pre-disposed to undergoing, abnormal or uncontrolled growth. The cell may be a cancerous cell with stem-cell like properties or a stem-cell with cancerous properties, for example uncontrolled proliferation or the capacity to differentiate into other cell types.

The cell may be a cell in culture or it may be a cell within a subject. The cell may be derived from any organism whose cells undergo autophagy, and in particular embodiments is a mammalian cell, including a mouse cell, a rat cell, a rabbit cell or a human cell.

A cell that is currently undergoing cancer therapy refers to a cell that is currently being treated with a cancer therapy regimen, including simultaneously with, overlapping with, or sequentially prior to or following the inhibition of expression of an Atg gene, provided that the benefit or effect of the cancer therapy treatment is ongoing in the cell concomitantly with the inhibition. Thus, "currently undergoing cancer therapy" includes cancer therapy that covers a greater or lesser period of time as the time period for which the expression of an Atg gene is to be inhibited, and which may or may not overlap with the time period for which the expression of an Atg gene is to be inhibited. In some instances, it may be beneficial to inhibit the expression of the Atg gene subsequent to the cancer treatment in a cell type that exhibits high levels of autophagy, in order to increase the effect of the present method.

In alternative aspects of the invention, the cancer therapy may be any one of a number of therapies given to a cell to treat, inhibit or prevent cancer and may for example include, in alternative embodiments, chemotherapy, endocrine therapy, radiation therapy and chemoradiation therapy. Chemotherapy refers to treatment with drugs or chemical compounds that target cancer cells. Endocrine therapy, also called hormone therapy, refers to treatment that removes, blocks, or adds hormones. Radiation therapy refers to the use of high-energy radiation from x-rays, gamma rays, neutrons, and other sources to target cancer cells. Radiation may be administered externally or it may be administered using radioactive material given internally. Chemoradiation therapy combines chemotherapy and radiation therapy. In some aspects of the invention, the cancer therapy may have a cytotoxic or cytostatic effect. The cancer therapy may also be a therapy that invokes or induces cyto-protective autophagy in the cell.

An endocrine therapy may involve administration of a compound that is typically administered to a cell and which reduces, down-regulates, minimizes, blocks, up-regulates or increases the activity or expression of one or more hormones. A chemotherapy may involve administration of a chemotherapeutic compound, which may have a cytotoxic or cytostatic effect, or which may induce a cyto-protective autophagy response in the cell. The chemotherapeutic agent or the endocrine therapeutic agent may be an agent that induces apoptosis, such as p53-dependent apoptosis, or that induces cell cycle arrest, including p53-dependent cell cycle arrest, in a cell that is abnormally proliferating or cancerous, even in the absence of inhibition of expression of an Atg gene. The chemotherapeutic agent or the endocrine therapeutic agent may be an agent that causes metabolic stresses, glucose imbalance, anti-angiogenic effects, even in the absence of inhibition of expression of an Atg gene.

A chemotherapy or endocrine therapy may comprise treatment with a DNA damaging agent or a genotoxic agent that can activate p53-dependent apoptosis or p53-dependent cell cycle arrest in a proliferating cell. The chemotherapy or endocrine therapy may involve, without limitation, administration of a chemotherapeutic agent or endocrine therapeutic agent comprising a small molecule, a peptide or a protein, an anthracycline, an alkylating agent, an alkyl sulfonate, an aziridine, an ethylenimine, a methylmelamine, a nitrogen mustard, a nitrosourea, an antibiotic, an antimetabolite, a folic acid analogue, a purine analogue, a pyrimidine analogue, an enzyme, a podophyllotoxin, a platinum-containing agent or a cytokine. Preferably, the chemotherapeutic agent or endocrine therapeutic agent is one that is known to be effective against the particular cancer and cell type.

In certain embodiments the chemotherapy comprises administration of cisplatin, Adriamycin (ADR), 5-fluorouracil (5-FU), etoposide, or camptothecin or a derivative or analog thereof.

In a particular embodiment the cancer therapy comprises administration of tamoxifen or a related taxane. Tamoxifen is an anti-estrogen used in the treatment and chemoprevention of breast cancer. Tamoxifen has been shown to induce autophagy in MCF7 human breast carcinoma cells (9) as well as in FM3A murine breast tumour cells (10). In MCF7 cells it is believed to be responsible for non-apoptotic type II cell death (11).

In another particular embodiment, the cancer therapy comprises radiation treatment.

An Atg gene is a gene involved in autophagy or in autophagosome formation, either directly or through regulatory associations. In various embodiments, the Atg gene is the gene encoding ULK2 (Atg1), ULK1, Atg2, APG3P (PC3-96 or Atg3), APG4B (Autophagin 1 or Atg4), APG4A (Autophagin 2 or AUTL2), Autophagin 3 (AUTL1), Autophagin 4 (AUTL4), APG5L (Atg5), Beclin 1 (BECN1 or Atg6), APG7 (Atg7), MAP1LC3B (Atg8), MAP1LC3A, GATE16 (GABARAPL2), GABARAP, Atg9 (APG9L1/2), APG10L (Atg10), APG12L (Atg12), APG16L (Atg16), mTOR, PIK3C3 (VPS34) or WIPI49 (Atg18). In various embodiments, the Atg is a human homologue or orthologue of an Atg gene, such as hAtg1, hAtg2, hAtg3, hAtg4, hAtg5, hAtg6, hAtg7, hAtg8, hAtg9, hAtg10, hAtg12, hAtg16 or hAtg18.

MAP1LC3B is the human orthologue of yeast autophagy gene ATG 8. ATG 8 is essential for the elongation of the "isolation membrane" which makes up the structure of the autophagosome and serves as an indicator for autophagy. Beclin 1 is the human orthologue of Yeast Autophagy gene ATG 6 and has shown to be a regulator of mammalian autophagy.

In a particular embodiment, the Atg gene is Beclin 1. In another particular embodiment, the Atg gene is Atg7. In another particular embodiment, the Atg gene is Atg5.

In selected embodiments of the invention, the cellular response to a cancer therapy is increased by inhibiting expression of an Atg gene. "Inhibiting expression" or "inhibition of expression" of an Atg gene refers in alternative embodiments to a variety of mechanisms for inhibiting, knocking down, down-regulating, disrupting, interrupting, reducing, limiting, blocking or preventing expression of the Atg gene.

Thus, the cell may be treated so as to inhibit expression of an Atg gene in the cell. Inhibition may be accomplished by treating or contacting the cell with an agent that inhibits the expression of an Atg gene. In alternative embodiments, such agents may include small molecules, nucleic acids, peptides, antibodies, or other gene inhibition/knock-down techniques.

The agent may be capable of being delivered internally to a cell, for example by active or passive transport into the cell, or by diffusion into the cell. For example, if the agent is a small molecule, it may be soluble in the cell membrane and thus able to permeate the cell.

The agent may also be modified to include a transport tag that will facilitate its transport into a cell. Specific transport tags may be used in order to direct the agent to be taken up by specific target cells. For example, the agent may be modified to include a galactose residue to increase uptake of the agent by hepatocytes. Where the agent is a peptide, inclusion of a sequence such as a membrane-translocating sequence that allows the peptide in which it is included to be transported into a cell, for example the penetratin sequence derived from the *Drosophila melanogaster* antennapedia homeodomain protein, facilitates the uptake of the agent by the cell. Alternatively, the agent may be included in a biomaterial which increases or induces uptake of the agent by the cell, for example, by encapsulating the agent in a liposome preparation.

Particularly, the agent may be a nucleic acid molecule capable of inhibiting expression of an Atg gene. The nucleic acid molecule may be, in various embodiments, a nucleic acid encoding a DNA enzyme, an antisense RNA, an siRNA or an aptamer.

In one embodiment, the agent comprises a DNA enzyme that targets the transcript of an Atg gene. A DNA enzyme is a magnesium-dependent catalytic nucleic acid composed of DNA that can selectively bind to an RNA substrate by Watson-Crick base-pairing and potentially cleave a phosphodiester bond of the backbone of the RNA substrate at any purine-pyrimidine junction (Santiago, F. S., et al., (1999) *Nat Med* 5: 1264-1269). A DNA enzyme is composed of two distinct functional domains: a 15-nucleotide catalytic core that carries out phosphodiester bond cleavage, and two hybridization arms flanking the catalytic core; the sequence identity of the arms can be tailored to achieve complementary base-pairing with target RNA substrates.

In some aspects of the invention, a DNA enzyme may be used that has complementary regions that can anneal with regions on the transcript of an Atg gene flanking a purine-pyrimidine junction, such that the catalytic core of the DNA enzyme is able to cleave the transcript at the junction, rendering the transcript unable to be translated to produce a functional protein from the Atg gene. In certain embodiments, the DNA enzyme is designed to cleave the Atg gene transcript between the A and the U residues of the AUG start codon.

Alternatively, the nucleic acid molecule comprises an antisense RNA. The antisense RNA molecule will contain a sequence that is complementary to the RNA transcript of an Atg gene, and which can bind to the Atg transcript, thereby reducing or preventing the expression of the Atg gene in vivo. The antisense RNA molecule will have a sufficient degree of complementarity to the target mRNA to avoid non-specific binding of the antisense molecule to non-target sequences under conditions in which specific binding is desired, such as under physiological conditions.

Alternatively, the nucleic acid molecule comprises an siRNA. siRNAs (short interfering RNAs) are double-stranded RNA (dsRNA) molecules that induce the sequence-specific silencing of genes by the process of RNA interference (RNAi) in multiple organisms, including humans (22). An siRNA typically targets a 19-23 base nucleotide sequence in a target mRNA.

Naturally occurring siRNAs tend to be 21-28 nucleotides in length and occur naturally in cells. However, synthetic siRNAs have been used to specifically target gene silencing in mammalian cells. Alternative aspects of siRNA technology include chemical modifications that increase the stability and specificity of the siRNAs, and a variety of delivery methods and in vivo model systems (reviewed in 22, 23). siRNA sequences can for example be designed using software algorithms that are commercially available. For example, the algorithm BLOCK-iT™ RNAi Designer (Invitrogen, California), can be used to select appropriate sequences for an siRNA directed against an Atg gene.

Thus, the siRNA molecule may be selected from a variety of double-stranded RNA molecules, including a self-complementary single-stranded molecule that can fold back on itself to form the double-stranded siRNA, which induces gene-specific RNA interference in a cell, leading to decreased or no expression of the Atg gene in vivo.

In one embodiment, the siRNA targets the Atg gene Beclin 1 and comprises the following sequence [SEQ ID NO.: 1]: GCU GUU UGG AGA UCU UAG AGC AAA U In one embodiment, the siRNA targets the Atg gene Beclin 1 and comprises the following sequence [SEQ ID NO.: 2]: GGA UGA UGAGCU GAA GAG UGU UGA A In one embodiment, the siRNA targets the Atg gene Beclin 1 and comprises the following sequence [SEQ ID NO.: 3]: UAU CUG UGC AUU CCU CAC AGA GUG G In one embodiment, the siRNA targets the Atg gene Beclin 1 and comprises the following sequence [SEQ ID NO.: 4]: AGC UGC UGU CGU UUA AAU UCA CUG U In one embodiment, the siRNA targets the Atg gene Beclin 1 and comprises the following sequence [SEQ ID NO.: 5]: UUC AAC ACU CUU CAG CUC AUC AUC C In one embodiment, the siRNA targets the Atg gene Atg7 and comprises the following sequence [SEQ ID NO.: 6]: GCU GGA UGA AGC UCC AAG GA CAU U In one embodiment, the siRNA targets the Atg gene Atg7 and comprises the following sequence [SEQ ID NO.: 7]: CCA AGG AUG GUG AAC CUC AGU GAA U In one embodiment, the siRNA targets the Atg gene Atg7 and comprises the following sequence [SEQ ID NO.: 8]: AAA CCU UUG AUC CAA ACC CAC UGG C In one embodiment, the siRNA targets the Atg gene Atg5 and comprises the following sequence [SEQ ID NO.: 9]: GAU CAC AAG CAA CUC UGG AUG GGA U In one embodiment, the siRNA targets the Atg gene Atg5 and comprises the following sequence [SEQ ID NO.: 10]: AUU CCA UGA GUU UCC GAU UGA UGG C In one embodiment, the siRNA targets the Atg gene Atg5 and comprises the following sequence [SEQ ID NO.: 11]: AAA CAA GUU GGA AUU CGU CCA AAC C In one embodiment, the siRNA targets the Atg gene Atg5 and comprises the following sequence [SEQ ID NO.: 12]: AUC CCA UCC AGA GUU GCU UGU GAU C In other embodiments, the siRNA consists of a sequence of any one of SEQ ID NOs.: 1 to 12. In other embodiments, the siRNA consists of a chemically modified sequence of any one of SEQ ID NOs.: 1 to 12, including the chemical modification of Invitrogen's proprietary siRNA technology, STEALTH™. In still other embodiments, the siRNA consists essentially of a sequence of any one of SEQ ID NOs.: 1 to 12. In still other embodiments, the siRNA consists essentially of a chemically modified sequence of a sequence of any one of SEQ ID NOs.: 1 to 12, including the chemical modification of Invitrogen's proprietary siRNA technology, STEALTH™. "Consists essentially of" or "consisting essentially of" means that the sequence includes one or more nucleotides at one or both ends of the described sequence, but that the additional nucleotide or nucleotides does not materially affect the siRNA's function of inhibiting expression of the target Atg gene. For example, the siRNA consisting of one of the above-mentioned sequences may have one, two, three, five or ten nucleotides at one or both ends of the described sequence, provided that such an siRNA still inhibits the expression of an Atg gene as described in the present method.

The siRNA may be further chemically modified. In certain embodiments, the siRNA is chemically modified using the STEALTH™ RNAi technology from Invitrogen (Invitrogen Corporation, Carlsbad, Calif., USA). STEALTH™ RNAi molecules have a proprietary chemical modification to ensure effective gene knockdown with higher specificity, greater stability and avoidance of stress response compared to traditional siRNA methods.

The above-described nucleic acid molecules may be synthesized using standard techniques known in the art, for example, standard phosphoramidite chemical ligation methods may be used to synthesize the nucleic acid molecule in the 3' to 5' direction on a solid support, including using an automated nucleic acid synthesizer. Alternatively, the nucleic acid molecule may be synthesized by transcribing a nucleic acid molecule encoding the desired nucleic acid molecule, or by using standard molecular cloning techniques including PCR methods as are known in the art. The nucleic acid molecule may be contained within a DNA or RNA vector, for delivery into a cellular expression system, for example, a viral vector. Suitable viral vectors include vaccinia viral vectors and adenoviral vectors. Standard molecular biology techniques are known in the art, and are described for example in Sambrook et al. ((2001) Molecular Cloning: a Laboratory Manual, 3$^{rd}$ ed., Cold Spring Harbour Laboratory Press).

Thus, the inhibition may be achieved by treating or contacting the cell with the nucleic acid molecule capable of inhibiting expression of an Atg gene so that the nucleic acid molecule is taken up by the cell, and is able to target and inhibit expression of the Atg gene in the cell, resulting in decreased or no expression of the functional protein encoded by the Atg gene.

As an alternative to delivery of an antisense RNA molecule, a DNA enzyme molecule or an siRNA molecule, the invention may involve delivery of a nucleic acid encoding such a molecule. In the case of the an antisense RNA or an siRNA, a DNA molecule, for example a DNA vector, encoding the antisense RNA or siRNA molecule may be delivered such that the antisense RNA or siRNA can be transcribed from the DNA vector once in the cell. Similarly, in the case of the DNA enzyme, an RNA viral vector encoding the DNA enzyme may be delivered to the cell, provided that viral vector also encodes sufficient molecular machinery to enable reverse transcription of the DNA enzyme, for example a reverse transcriptase enzyme.

The nucleic acid molecule capable of inhibiting expression of an Atg gene may be effectively delivered to the cell by a variety of methods. Such methods include liposomal encapsulation and delivery, vector-based gene transfer, fusion to peptide or immunoglobulin sequences for enhanced cell targeting and other techniques.

A variety of liposomes and liposomal encapsulation methods may be used in the invention. Briefly, liposomes are spherical vesicles made of an artificial lipid bilayer and may be used to encapsulate a biological or therapeutic agent for delivery to a cell, such as the described nucleic acid molecules capable of inhibiting expression of an Atg gene. The lipid bilayer of the liposome can fuse with the lipid membrane of a cell, allowing for delivery of the liposome contents to the cell. For example, where the agent is a nucleic acid, the agent may be encapsulated in a stable nucleic acid-lipid particle (SNALP), as is described in Dykxhoorn et al., *Gene Therapy* (2006) 13, 541-552. SNALP technology consists of a lipid bilayer containing a mixture of cationic and fusogenic lipids. (see also: Morrissey D V, et al. *Nat Biotechnol* 2005; 23(8): 1002-7; and Santel A, et al. *Gene Therapy* (2006) September; 13(18):1360-70.)

Liposomes can be manufactured by sonicating lipids in an aqueous solution. Low shear rates create multilamellar vesicles, which have many lipid layers. Continued high-shear sonication tends to form smaller unilamellar liposomes. In this technique, the liposome contents are the same as the contents of the aqueous phase. In order to avoid detection by the cells of reticuloendothelial system (RES), liposomes may be constructed using polyethylene glycol (PEG) as a coating, which allows for longer circulatory life for the drug delivery mechanism. As well, the liposomes may have a ligand attached to the surface of the liposome in order to enable binding to a target cell via a specific cell surface receptor or other surface molecule.

Inhibition of expression of an Atg gene to increase a cellular response to cancer therapy is useful in vitro and in vivo, and may be used in the treatment or inhibition of cancer. Thus, in another aspect, there is provided a method of treating cancer comprising administering to a subject an effective amount of an agent that is capable of inhibiting expression of an Atg gene in combination with a cancer therapy.

In alternative aspects, a cancer to be treated may be one or more of a variety of cancers, including breast cancer, liver cancer, ovarian cancer, gastric cancer, bladder cancer, colon cancer, prostate cancer, lung cancer, nasopharyngeal carcinoma, cervical carcinoma, skin cancer, brain cancer including neuroblastoma and glioma, solid tumours, hematologic malignancies including leukemia and lymphoma, or head and cancer including squamous cell carcinoma of the lip, mouth, nasal cavity, pharynx, larynx, thyroid, paranasal sinuses, salivary glands or cervical lymph nodes of the neck. In a particular embodiment, the cancer is breast cancer. In another particular embodiment, the cancer is liver cancer. In yet another particular embodiment, the cancer is ovarian cancer.

The term "treating" cancer refers to an approach for obtaining beneficial or desired results, including clinical results. Beneficial or desired clinical results can include, but are not limited to, alleviation or amelioration of one or more symptoms or conditions, diminishment of extent of disease, stabilization of the state of disease, prevention of development of disease, prevention of spread of disease, delay or slowing of disease progression, delay or slowing of disease onset, amelioration or palliation of the disease state, and remission (whether partial or total). "Treating" can also mean prolonging survival of a subject beyond that expected in the absence of treatment. "Treating" can also mean inhibiting the progression of disease, slowing the progression of disease temporarily, or halting the progression of the disease permanently.

The subject for treatments of the invention may for example bean animal in need of treatment for a cancer, such as a mammal, including a human. In alternative embodiments, the subject may for example be a subject who has cancer, who is being treated for cancer, who is diagnosed as having cancer, who is predisposed to developing cancer, in whom cancer is to be treated, or in whom cancer is to be prevented.

In the context of various aspects of the invention, treatments "in combination" with a therapy, such as a cancer therapy, means that the administration of the agent capable of inhibiting expression of an Atg gene occurs in a time period during which a therapy is administered to the subject, for example simultaneously with, overlapping with, or sequentially prior to or following the administration of the cancer therapy treatment, provided that the benefit or effect of the cancer therapy treatment is ongoing in the cell concomitantly with the administration of the agent capable of inhibiting expression of an Atg gene. The administration of the agent capable of inhibiting expression of an Atg gene and the administration of the therapy may occur simultaneously or sequentially, and the respective time period for each may be conterminous, overlapping or sequential. The administration of the agent capable of inhibiting expression of an Atg gene and the administration of the therapy each may be achieved in one or more discrete treatments or may be performed continuously for a given time period required in order to achieve the desired result.

In various aspects of the invention, an effective amount of an agent capable of inhibiting expression of an Atg gene is administered to a subject. In this context, the term "effective amount" means an amount effective, at dosages and for periods of time necessary to achieve the desired result, for example, to treat the specific cancer.

In alternative embodiments, an agent may be administered to a subject using a variety of techniques. For example, the agent may be administered systemically, which includes by injection including intramuscularly or intravenously, orally, sublingually, transdermally, subcutaneously, internasally. Alternatively, the agent may be administered directly at a site at which the cancer is located. Delivery to the site includes topical administration, injection to the site, or surgical implantation, for example at a site of a tumour.

The concentration and amount of the agent capable of inhibiting expression of an Atg gene to be administered will typically vary, depending on the cancer, the type of cell associated with the cancer, the type of agent that is administered, the mode of administration, and the age and health of the subject.

To aid in administration, the agent capable of inhibiting expression of an Atg gene may be formulated as an ingredient in a pharmaceutical composition, including in a liposome preparation.

Therefore, in a further aspect, there is provided a pharmaceutical composition comprising an agent capable of inhibiting expression of an Atg gene, and a pharmaceutically acceptable diluent. The compositions may routinely contain pharmaceutically acceptable concentrations of salt, buffering agents, preservatives and various compatible carriers. Agents capable of inhibiting expression of an Atg gene may for example be formulated in a physiological salt solution.

The proportion and identity of the pharmaceutically acceptable diluent may be determined by the chosen route of administration, compatibility with live cells, and standard pharmaceutical practice. Generally, the pharmaceutical composition will be formulated with components that will not significantly impair the biological properties of the agent capable of inhibiting expression of an Atg gene.

The agent capable of inhibiting expression of an Atg gene may for example be combined or co-administered with one or more such agents in any number of combinations, for example one or more agents that inhibit expression of a particular Atg gene and/or one or more agents that inhibit expression of different Atg genes.

The agent capable of inhibiting expression of an Atg gene may further be formulated together with other compounds or agents which may enhance delivery of the active agent capable of inhibiting expression of an Atg gene, including for example a cyclodextrin.

The pharmaceutical composition may additionally contain other therapeutic agents useful for treating the particular proliferative disorder, for example an endocrine therapeutic or chemotherapeutic agent.

Thus, in particular embodiments, the pharmaceutical composition comprises one or more siRNA, including a STEALTH modified siRNA, directed against Beclin 1, Atg5 or Atg7, and may further comprise the one or more siRNA encapsulated in a liposome, including a liposome using SNALP technology, and may further comprise tamoxifen or a related taxane.

The pharmaceutical composition can be prepared by methods for the preparation of pharmaceutically acceptable compositions suitable for administration to patients, such that an effective quantity of the agent capable of inhibiting expression of an Atg gene, and any additional active substance or substances, is combined in a mixture with a pharmaceutically acceptable vehicle. Suitable vehicles are described, for example, in Remington's Pharmaceutical Sciences (Remington's Pharmaceutical Sciences, Mack Publishing Company, Easton, Pa., USA 1985). On this basis, the pharmaceutical compositions include, albeit not exclusively, solutions of agent capable of inhibiting expression of an Atg gene, in association with one or more pharmaceutically acceptable vehicles or diluents, and contained in buffer solutions with a suitable pH and iso-osmotic with physiological fluids.

The pharmaceutical composition may be administered to a patient in a variety of forms depending on the selected route of administration, as will be understood by those skilled in the art. The composition of the invention may be administered topically, surgically or by injection either systemically or to the desired site.

Solutions of the agent capable of inhibiting expression of an Atg gene may be prepared in a physiologically suitable buffer. Under ordinary conditions of storage and use, these preparations contain a preservative to prevent the growth of microorganisms, and that will maintain the function of the agent capable of inhibiting expression of an Atg gene. A variety of procedures and ingredients for the selection and preparation of suitable formulations are described, for example, in Remington's Pharmaceutical Sciences and in The United States Pharmacopeia: The National Formulary (USP 24 NF19) published in 1999.

The dose of the pharmaceutical composition that is to be used depends on the particular condition being treated, the severity of the condition, the individual patient parameters including age, physical condition, size and weight, the duration of the treatment, the nature of concurrent therapy (if any), the specific route of administration and other similar factors that are within the knowledge and expertise of the health practitioner. These factors are known to those of skill in the art and can be addressed with minimal routine experimentation.

In various embodiments, the invention involves the use of a nucleic acid molecule comprising a DNA enzyme, an antisense RNA or an siRNA, to inhibit expression of an Atg gene.

In specific embodiments, the nucleic acid molecule comprises an siRNA comprising the sequence of any one of SEQ ID NOs.: 1 to 12, or an siRNA consisting essentially of the sequence of any one of SEQ ID NOs.: 1 to 12, or an siRNA consisting of the sequence of any one of SEQ ID NOs.: 1 to 12, including an siRNA that has been chemically modified, as described above.

Also presently contemplated are uses of such agents, including uses for inhibiting expression of an Atg gene in a cell currently undergoing the cancer therapy in order to increase a cellular response to a cancer therapy and for treating cancer in combination with a cancer therapy. Also contemplated is use of such agents in the preparation of medicaments for the above-mentioned uses.

The invention is further exemplified by the following non-limiting examples.

EXAMPLES

Example 1

A FACS based strategy coupled with quantitative mRNA and protein analysis is employed to quantify the effect of inhibition of autophagy at the molecular level in cancer treatment models. In addition, siRNA based knockdown is used to disrupt autophagy genes thereby allowing autophagy to be assessed selectively.

The results indicate that inhibition of autophagy in tamoxifen treated breast carcinoma cells leads to an increase in cell death.

Materials and Methods

Atg gene-siRNA in breast carcinoma cell line: The human MCF7 breast carcinoma cell line is used in these studies for several reasons. First, MCF7 cells undergo autophagy following treatment with tamoxifen (9) and irradiation (11). Second, monodansylcadaverine (MDC) staining in tamoxifen-treated MCF7 cells correlates with autophagic activity (13) and thus provides a useful autofluorescent marker that can be used in addition with the autophagosome marker GFP-LC3 and the lysosomal stain LysoTracker® Green (LT-G) (Molecular Probes). Third, MCF7 cells can be transfected efficiently with short interfering (si)-RNA (12 and 19). Thus, MCF7 cells were treated with tamoxifen (9) or irradiation (16) as described, and transfected with siRNA targeting the hAtg genes. Levels of autophagy, cell viability, and apoptosis will be compared to control cells as described below.

RNAi system: We employed the STEALTH™ RNAi technology from Invitrogen (Invitrogen Corporation, Carlsbad, Calif., USA) for our studies. STEALTH™ RNAi molecules are 25 bp RNA oligonucleotides with a proprietary chemical modification to ensure effective gene knockdown with higher specificity, greater stability and avoidance of stress response compared to traditional siRNA methods. Three STEALTH™ RNAi duplex molecules (Invitrogen) along with a scrambled siRNA duplex (Invitrogen) per gene will be used. Three different siRNA molecules per gene were used in order to help identify any false positive results of siRNA on cell viability due to off-target gene silencing effects. STEALTH™ RNAi were transfected using Lipofectamine 2000 (Invitrogen). Transfection efficiencies were assayed by adding BLOCK-IT™ fluorescent Oligos (FITC-labeled dsRNA oligomers) both in test and in control cultures (Invitrogen). Gene knockdown was assessed by QRT-PCR for the targeted hAtg genes as well as for PKR and OSA-1 to elucidate any interferon mediated stress response, every 24 hour for up to 7 days (12). GAPDH and cytoplasmic β-actin were used as endogenous controls.

The RNAi experiment involved seeding $5 \times 10^3$ MCF7 cells/well in 96 well format in the presence of OPTI-MEM™ media (Invitrogen) with 4% dextran charcoal stripped serum with no antibiotics and no phenol red (9). The following day 5 pM of siRNA complexed with Lipofectamine 2000™ in OPTI-MEM™ medium with no antibiotics, no phenol red and no serum were added. Following an incubation of 4 hour with the siRNA the cells were then treated with 1 μM and 5 μM Tamoxifen. All siRNA and Tamoxifen treatments were performed in triplicate. Cell survival was assessed every 24 hours for the next 6 days as described below.

Assays for autophagy and cell viability: We used flow cytometry based methods and microscopy to analyze autophagy levels. Cells were stained with MDC and LT-G and first analyzed manually by fluorescence microscopy and then by flow cytometry using a BD® flow cytometer (FACSVANTAGE™ SE, BD, TFL FACS Facility, BCCRC). Analyses indicated that FACS can detect and sort cells from Tamoxifen treated MCF7 cells into two distinct populations based on high and dim MDC and LTG fluorescence. To confirm that these two populations represent a functional difference in autophagy levels, RNA and protein from these FACS sorted cell were subjected to QRT-PCR for the MAP1LC3b gene, a commonly accepted marker for autophagy (16). In addition, the two populations were analyzed by Transmission Electron Microscopy (TEM) for the presence of autophagosomes (9). The FACS sorted autophagy positive and negative cells were re-plated and subjected to cell proliferation assays and siRNA treatment to further allow characterization of these autophagy enriched cells in relation to their growth potential, drug resistance and susceptibility to autophagy inhibition when compared to low autophagy exhibiting cells.

Cell viability following siRNA and Tamoxifen treatment was assessed by employing the cell viability reagent, WST-1 (Roche) every 24 hours for up to 06 days. WST-1 is a tetrazolium salt that can be cleaved only by metabolically active cells; the cleavage product is directly quantitated by measuring sample absorbance (BioTek Powerwave Spectrophotometer, Genome Sciences Centre). In addition, percent cell viability and percent cell death was determined by using a VI-CELL™ counter (Beckman Coulter, Terry Fox Lab's FACS Facility) and/or INCell™ Analyser T1000.

Assays for Apoptosis and Apoptosis Pathways: To determine the involvement of apoptosis and apoptosis related pathways in these cells, at least one siRNA molecule per gene with maximum effect on cell viability and minimum off-target effects was further analyzed by assessing the role of various caspases. Cells undergoing apoptosis were measured using Annexin-V (Molecular Probes) and assays for Caspase 3, 7, 8 and 9 (Roche and BioRad) activity was performed by fluorimetric assay in 96 well format.

To further elucidate which apoptosis genes and or pathways are becoming active in the dying cells, QRT-PCR based Human Apoptosis $RT^2$ Profiler™ PCR Array (SuperArray Bioscience Cooperation) and/or custom RT-PCR arrays were employed. The Profiler™ Array profiles the expression of 84 key genes involved in apoptosis or programmed cell death. The array includes the TNF ligands and their receptors, members of the bcl-2, caspase, IAP, TRAF, CARD, death domain, death effector domain, and CIDE families, as well as genes involved in the p53 and ATM pathways.

Irradiated MCF7 cells. Cells were irradiated by using a X-ray irradiator (Pantak, Seifert, X-RAD 320, Medical Biophysics, BCCRC) with a dose of 2 and 3 Gray, at a rate of 2.5 Gy/min as described previously (16). The experimental design as outlined for Tamoxifen treated MCF7 cells was also followed for cells irradiated. In addition, clonogenic assays for these cells were performed as described previously (16).

TABLE 1

HUMAN AUTOPHAGY-RELATED GENES

| ATG name | Gene name (human) | Chromosome location | LocusLink ID |
|---|---|---|---|
| ATG1 | ULK2 (Unc-51-Like Kinase 2) | 17p11.2 | 9706 |
|  | ULK1 (Unc-51-Like Kinase 1) | 12q24.3 | 8408 |
| ATG2 |  |  |  |
| ATG3 | APG3P; PC3-96 protein | 3q13.2 | 64422 |
| ATG4 | APG4B; Autophagin 1 | 2q37.3 | 23192 |
|  | APG4A; Autophagin 2; AUTL2 | Xq22.3 | 115201 |
|  | Autophagin 3; AUTL1 | 1p31.3 | 84938 |
|  | Autophagin 4; AUTL4 | 19p13.2 | 84971 |
| ATG5 | APG5L | 6q21 | 9474 |
| ATG6 | BECN1 (Beclin1) | 17q21.31 | 8678 |
| ATG7 | APG7, NM_006395 | 3p25.3 | 10533 |
| ATG8 | MAP1LC3A | 20q11.22 | 84557 |
|  | MAP1LC3B | 16q24.2 | 81631 |
|  | GATE16, GABARAPL2 | 16q23.1 | 11345 |
|  | GABARAP | 17p13.1 | 11337 |
| ATG9 | APG9, NM_024085 | 2q35 | 79065 |
| ATG10 | APG10L | 5q14.1-.2 | 83734 |
| ATG12 | APG12L | 5q22.3 | 9140 |
| ATG16 | APG16L, NM_030803 | 2q37.1 | 55054 |
| PIK3C3 | PIK3C3, VPS34 | 18q12.3 | 5289 |
| ATG18 | ATG18, WIPI49 |  |  |

Human gene names, chromosomal locations, AFFY IDs, and Locus Link IDs from Ensembl v19 (www.ensembl.org).
ATG name, other yeast gene names, and function from Klionsky et al., Dev Cell, 2003 and Mixushima et al., Cell Struc Fun, 2002, unless indicated otherwise.

Results

Results showing the efficacy of knockdown of various human autophagy-related genes with methods and compositions of the invention are shown in FIGS. 1 through 7.

FIG. 1. Certain siRNAs (and their nucleic acid sequences) useful for inhibiting the expression of the corresponding human autophagy-related genes and improving the therapeutic efficacy of endocrine therapy, chemotherapy or radiation therapy in cancer, as well as scrambled controls.

FIG. 2. Detection of autophagy by MDC in a time course assay. Tamoxifen (10-6 M) treated MDC stained MCF-7 cells were analysed by FACS. A1, B1 and C1 display the histograms from treated and un-treated cells at 24, 48 and 72 hr respectively. X-axis denotes MDC fluorescent intensity and Y-axis denotes the cell number. Cells below a fluorescent threshold as marked by a gate were referred to as MDC (−), where as cell above were MDC (+). A2, B2 and C2 show the percentage of cells in MDC (−) and MDC (+) gates in the control and treated cell populations at 24, 48 and 72 hr respectively. Data shown is representative of three independent experiments.

FIG. 3. Detection of autophagy by MDC and LysoTracker Green (LTG) in varying Tamoxifen concentration at 72 hr. A1 and B1 are the histograms showing un-treated, 1×10-6 M and 5×10-6 M tamoxifen treated MCF-7 cells stained for MDC and LTG respectively. In histogram A1 MDC fluorescent intensity on the X-axis is plotted against the cell number on the Y-axis. In histogram B1 LTG fluorescent intensity on the X-axis is plotted against the cell number on the Y-axis. Cells below a fluorescent threshold as marked by a gate were referred to as MDC (−) or LTG (−), whereas cells above were MDC (+) or LTG (+). A2 shows the percentage of cells in MDC (−), MDC (+) gates in the control and treated cell population, whereas B2 shows the same for LTG staining. Data shown is representative of three independent experiments.

Figure 4:
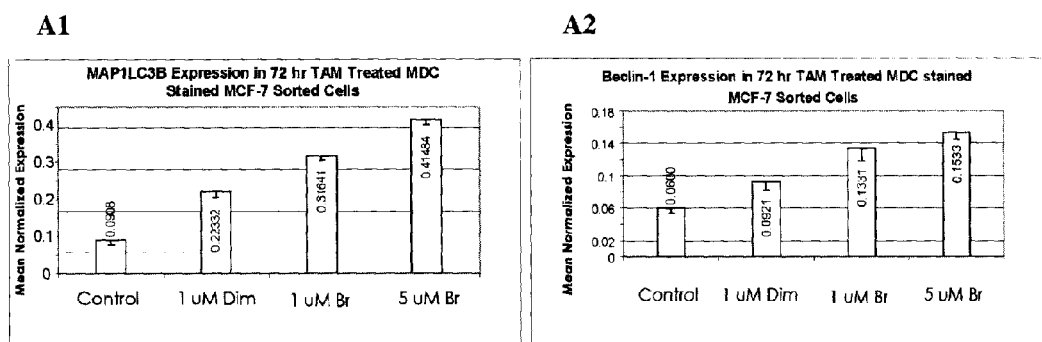
FIG. 4 is graphs showing the results of quantitative RT-PCR analysis of MAP1LC3B and Beclin 1 transcripts in Tamoxifen treated FACS sorted MCF-7 cells.

FIG. 4. Quantitative RT-PCR Analysis of MAP1LC3B and Beclin 1 Transcripts in Tamoxifen Treated FACS Sorted MCF-7 Cells. 1 and 5×10-6 M tamoxifen treated MCF-7 cells corresponding to MDC (−) and MDC (+) gates were FACS sorted and analysed for MAP1LC3B and Beclin 1 transcripts. The bar graphs in A1 and A2 represent expression levels of 72 hr tamoxifen treated cells for MAP1LC3B and Beclin 1 respectively.

Figure 5:
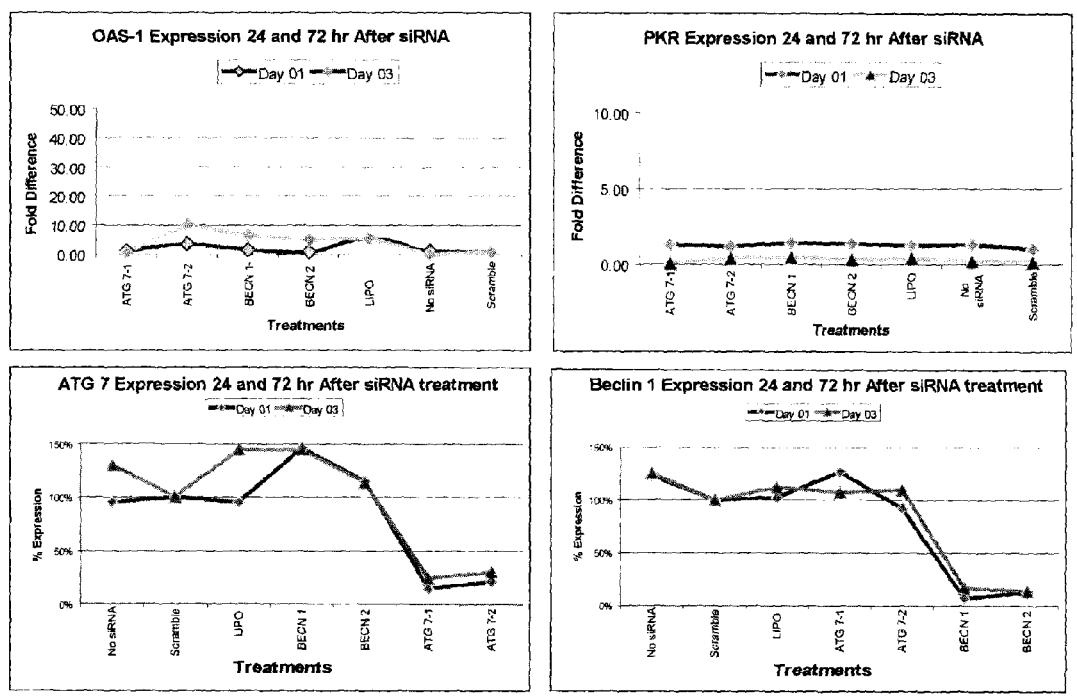
FIG. 5 is graphs showing the results of quantitative RT-PCR analysis of OAS-1, PKR, ATG7 and Beclin 1 transcripts in siRNA treated MCF-7 cells at 24 and 72 hr.

FIG. 5. Quantitative RT-PCR Analysis of OAS-1, PKR, ATG 7 and Beclin 1 Transcripts in siRNA Treated MCF-7 Cells at 24 hr and 72 hr. Upper panel shows expression profiles in fold difference for Interferon mediated stress responding genes OAS-1 and PKR respectively. Each gene is profiled at 24 and 72 hr post siRNA treatment. Bottom panel represent expression profiles for autophagy genes ATG 7 and beclin 1 after 24 hr and 72 hr of siRNA gene knockdown respectively. Each gene panel contains the following; No siRNA (no treatment), one scrambled siRNA, Lipo (lipofectamine only), two beclin siRNAs and two Atg7 siRNAs. Fold differences were calculated by dividing the mean expression values by their corresponding controls respectively (upper panel, data not shown) and percent expression was calculated by dividing the mean expression values by their corresponding scramble siRNA (lower panel, data not shown).

Figure 6:
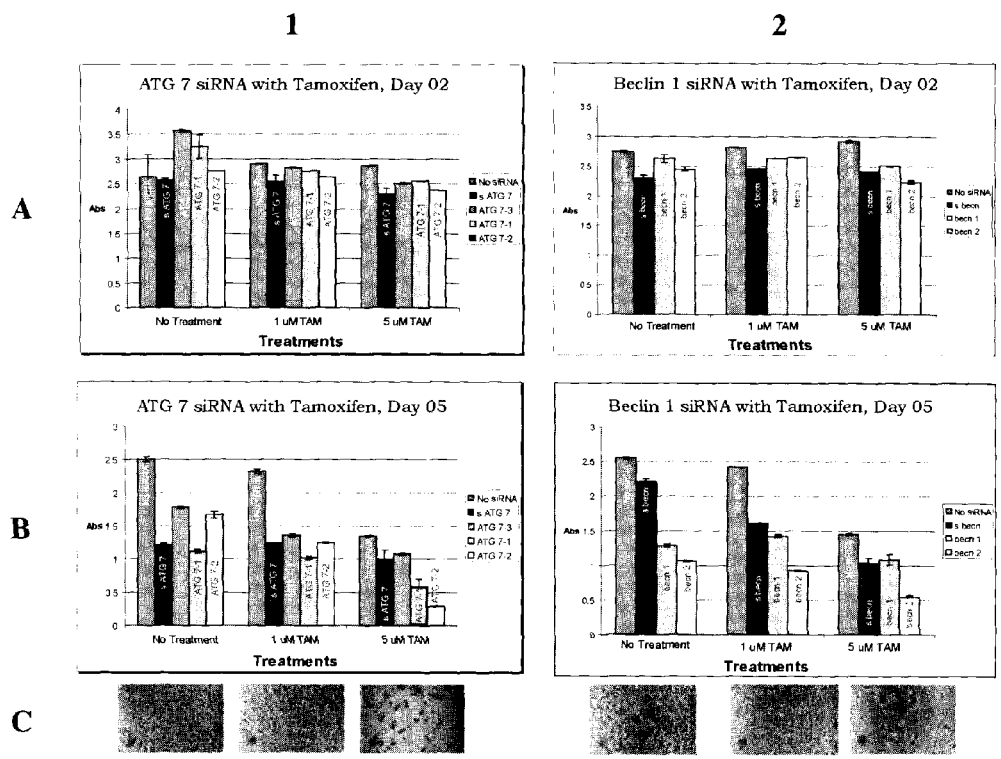
FIG. 6 is graphs depicting the effect of siRNA inhibition on tamoxifen treated MCF-7 cells as measured by WST-1 assay, and micrographs of cells treated with Atg7 or Beclin 1 siRNAs and tamoxifen.

FIG. 6. Effect of siRNA inhibition on Tamoxifen treated MCF-7 cells by WST-1 Assay. Panels A1 and A2 are beclin 1 and ATG 7 siRNA treated cells on Day 02 of Tamoxifen treatment. X-axis denotes un-treated, 1×10-6 M and 5×10-6 M tamoxifen treated MCF-7 cells. Each siRNA panel for beclin 1 and Atg 7 siRNA treatments contains the following: No siRNA (no treatment), scrambled siRNA (scrambled beclin 1 or Atg7 siRNA), and two and three siRNA molecules per gene (for beclin 1 and for Atg7 respectively). Panels B1 and B2 are the same at Day 05 of Tamoxifen treatment. Results indicate that cells treated with ATG7-2 siRNA and beclin 1-2 siRNA greatly increase the efficacy of 5×10-6 M tamoxifen by day 5 as seen in the corresponding image of the cells (C1 and C2).

Figure 7:
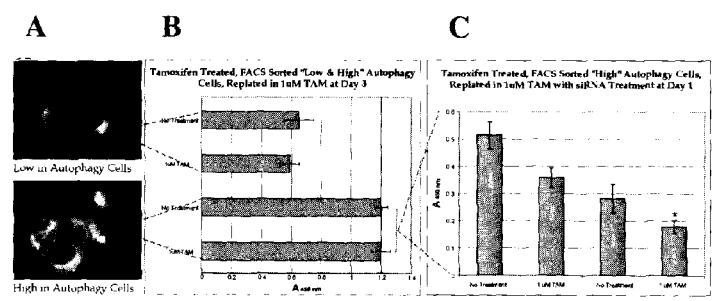
FIG. 7 is fluorescence micrographs of tamoxifen treated MCF-7 cells and graphs depicting the profiling of cells sorted on the basis of fluorescent intensity.

FIG. 7. Profiling of cells sorted on the basis of Fluorescent intensity. Panel A shows tamoxifen (1×10-6 M) treated, FACS sorted MCF-7 cells at 72 hr based on dim (Low Autophagy) and bright MDC fluorescence (High Autophagy). The dim and the bright populations correlate with the (−) and the (+) gates shown in FIGS. 2 and 3. Panel B: FACS sorted 72 hour tamoxifen (1×10-6 M) treated MCF-7 cells were re-plated and re-treated with tamoxifen (Y-axis) for 3 days. The Growth profile following treatment for these "Low & High" autophagy cells is indicated by WST-1 assay (X-axis), which demonstrates a two fold increase in viability for the "High" autophagy cells. Panel C: FACS sorted 72 hour tamoxifen (1×10-6 M) treated MCF-7 cells were re-plated, treated with 1 uM tamoxifen and beclin 1 siRNA for 24 hr. Results indicate that cells with "high autophagy" fare poorly upon inhibiting autophagy in combination with tamoxifen (C *) only after 24 hr, thereby compromising the growth advantage as seen in panel b.

Example 2

MDC (monodansylcadaverine): MDC is a lysosomotropic agent which preferentially labels autophago-lysosomes and some autophagosomes. It is believed that the specificity of MDC staining of autophagolysosomes depends on some kind of interaction between MDC and the lipid molecules, which are abundant in autophagolysosomes.

MAP1LC3B & Beclin 1: MAP1LC3B is the human orthologue of Yeast autophagy gene ATG 8. ATG 8 is essential for the elongation of the "isolation membrane" which makes up the structure of the autophagosome and serves as an indicator for autophagy. Our analysis reveals that the expression level of MAP1LC3B correlates with an increase in autophagy as detected by an increase in MDC signal. Beclin 1 is the human orthologue of Yeast Autophagy gene ATG 6 and has been shown to be a regulator of mammalian autophagy.

Figure 8:
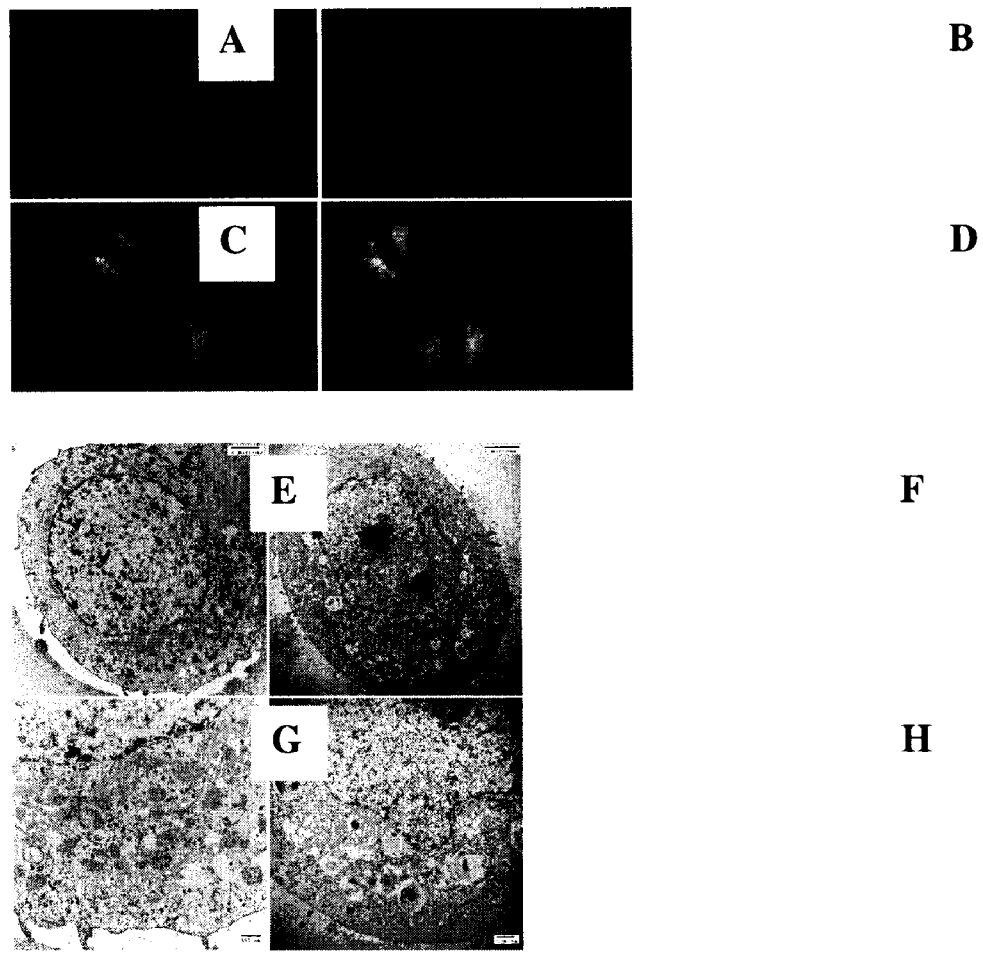
FIG. 8 is micrographs of MCF-7 cells treated with tamoxifen, stained with MDC or LC3-GFP.

FIG. 8. Tamoxifen induces autophagy in MCF-7 cells: A. MCF-7 control cells. B. MCF-7 cells treated with 10-6 M tamoxifen. In panels A, B, & D, cells are stained with the autolysosomal marker, MDC, detected as punctate staining (e.g. arrows in B).

In panels C and D, autophagy is detected by LC3-GFP localization. C. Punctate GFP-LC3 in transient transfected MCF7 cells treated with TAM. D. GFP-LC3 and MDC co-staining shows that MDC correlates with autophagy (LC3-GFP is bound to autophagosomal membranes). In panel E-H, TEM analyses indicate that autolysosomes are abundant in tamoxifen treated MCF7 cell sorted MDC (+) populations but not untreated MCF7 cells. Representative image of an untreated MCF7 cell is shown in (E) with a magnified view of the same cell in (G). Panels (F) and (H) show a cell treated with 5 uM tamoxifen (72 hrs). Numerous autolysosomes (e.g. arrows) are evident.

Figure 9:
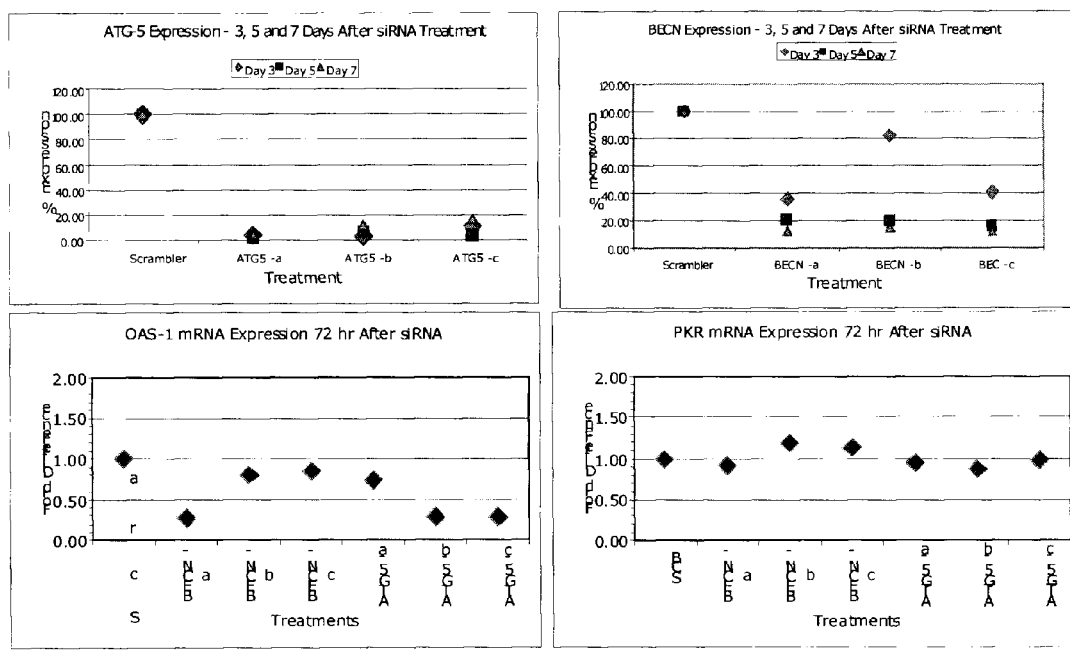
FIG. 9 is graphs depicting the results of quantitative RT-PCR analysis of OAS-1, PKR, ATG5 and Beclin 1 transcripts in siRNA treated MCF-7 cells.

FIG. 9. Quantitative RT-PCR Analysis of OAS-1, PKR, ATG 7 and Beclin 1 Transcripts in siRNA Treated MCF-7 Cells: Upper panels show expression profiles for autophagy genes ATG 5 and beclin 1 after days 3, 5 and 7 of the respective gene knockdown by siRNA. Each gene panel contains the following: One scrambled siRNA, three Atg5 siRNAs or three beclin 1 siRNAs. Bottom panels represent expression profiles in fold difference for Interferon mediated stress responding genes, OAS-1 and PKR. Each gene is profiled at 24 hr post siRNA treatment. Fold differences were calculated by dividing the mean expression values by their corresponding controls respectively (data not shown) and percent expression was calculated by dividing the mean expression values by their corresponding scramble siRNA (data not shown).

Figure 10:
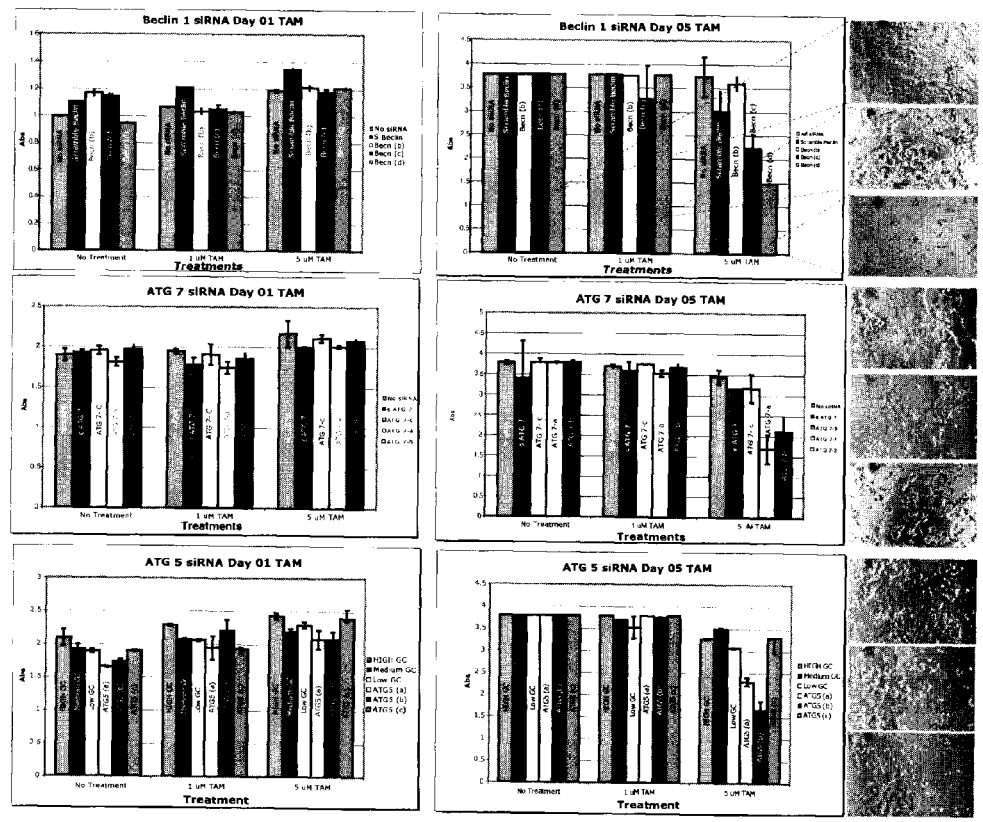
FIG. 10 is graphs showing the effect of siRNA inhibition on tamoxifen treated MCF-7 cells measured by WST-1 assay.

FIG. 10. Effect of siRNA inhibition on Tamoxifen treated MCF-7 cells by WST-1 Assay: Panels A1, A2 and A3 are beclin 1, ATG7 and ATG5 siRNA treated cells on Day 01 of Tamoxifen treatment. X-axis denotes untreated, 1×10-6 M and 5×10-6 M tamoxifen treated MCF-7 cells. Each siRNA panel for beclin 1, ATG7 siRNA and ATG5 treatments contains the following: No siRNA (no treatment), scrambled siRNA (scrambled beclin 1, scrambled Atg7 or High, Medium and Low universel GC control scramblers), and three unique siRNAs per gene (Y-axis denotes Absorbance). Panels B1, B2 and B3 are the same at Day 05 of Tamoxifen treatment. Results indicate that cells treated with beclin-c & d siRNA, ATG7-a & b siRNA and ATG5-a & b siRNA greatly increase the efficacy of 5×10-6 M tamoxifen by day 5 as seen in the corresponding image of the cells (C).

Figure 11:
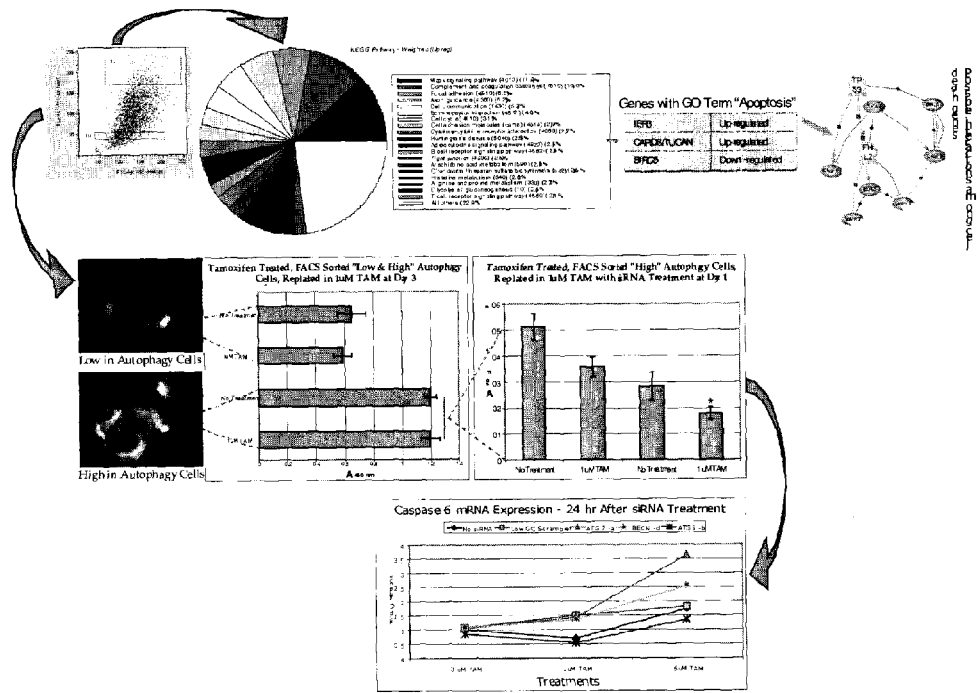
FIG. 11 is a depiction of the profiling of cells sorted on the basis of fluorescence intensity, after treatment with tamoxifen.

FIG. 11. Profiling of cells sorted on the basis of Fluorescence intensity: Panel A shows a typical FACS florescent profile of tamoxifen (1 or 5×10-6 M) treated, cells at 72 hr, which are FACS sorted based on dim (Low Autophagy) and bright MDC fluorescence (High Autophagy). The dim and the bright populations also correlate with the (−) and the (+) gates shown in FIG. 3. RNA isolated from FACS sorted 72 hour control and tamoxifen (1×10-6 M and 5×10-6 M) treated MCF-7 cells were subjected to Affymetrix gene chip analysis. Panel B: Genes showing a minimum 2 fold difference with a P value of <0.01 were grouped according to various cellular pathways as shown in the pie diagram. Genes with the GO Term "Apoptosis" are shown in table C. Panel D: A pathway was constructed which shows the shortest paths between the differentially expressed genes identified.

Panels E: Show tamoxifen (1×10-6 M) treated, FACS sorted MCF-7 cells at 72 hr based on dim (Low Autophagy) and bright MDC fluorescence (High Autophagy). The FACS sorted 72 hour tamoxifen (1×10-6 M) treated MCF-7 cells were re-plated and re-treated with tamoxifen (Y-axis) for 3 days. The Growth profile following treatment for these "Low & High" autophagy cells is indicated by the WST-1 assay (X-axis), which demonstrates a two fold increase in viability for the "High" autophagy cells.

Panel F: FACS sorted 72 hour tamoxifen (1×10-6 M) treated MCF-7 cells were re-plated, treated with 1 uM tamoxifen and beclin 1 siRNA for 24 hr. Results indicate that cells with "high autophagy" fare poorly following autophagy knockdown in combination with tamoxifen (F*) after 24 hr, thereby compromising the viability advantage observed earlier. Panel G: We have initiated an investigation of the molecular mechanism of cell death following combined autophagy gene –siRNA and tamoxifen treatment. An example of the QRT-PCR profile of caspase 6, in the dying TAM+siRNA treated cells is shown here.

Example 3

Figure 12:
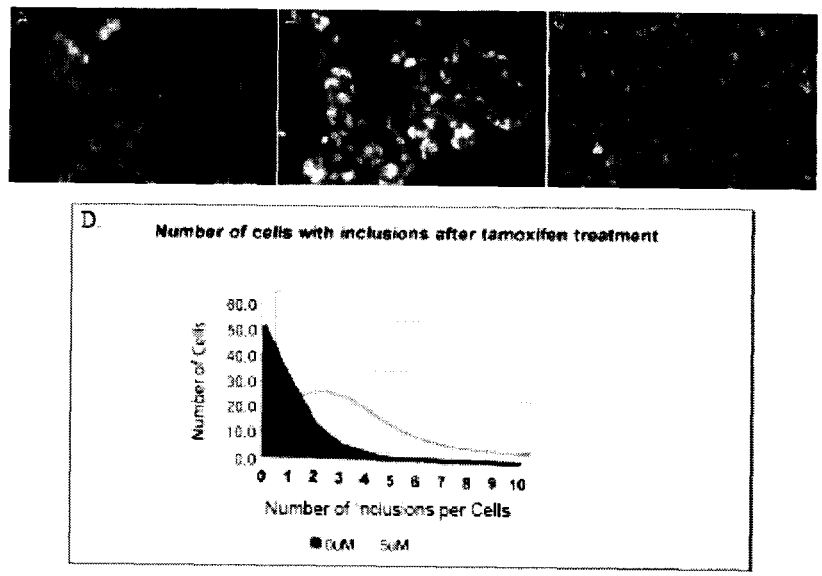
FIG. 12 is micrographs of MCF-7 cells treated with or without tamoxifen and a graph showing the results of FACS analysis.

FIG. 12. Measuring MDC-positive structures using the INCell Analyzer. Panel A is untreated (control) MCF7 cells, Panel B is 5 uM tamoxifen treated MCF7 cells, and Panel C shows the InCell Analyzer program running the "cell inclusion" algorithm to identify the number of MDC-positive inclusions per cell. Panel D illustrates the results of such an analysis conducted on triplicate samples.

Figure 13:
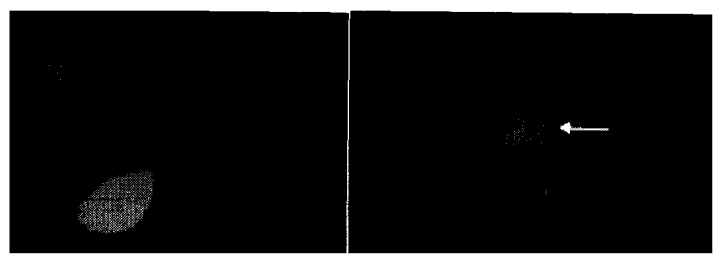
FIG. 13 is fluorescence micrographs of cells exhibiting or not exhibiting autophagy, using the marker GFP-LC3.

FIG. 13. Autophagy detection by GFP-LC3 localization. Left: Diffuse GFP staining correlates with no autophagy (GFP-LC3 is cytoplasmic). Right: Punctate GFP staining correlates with autophagy (GFP-LC3 is bound to autophagosomal membranes; arrow).

Figure 14:
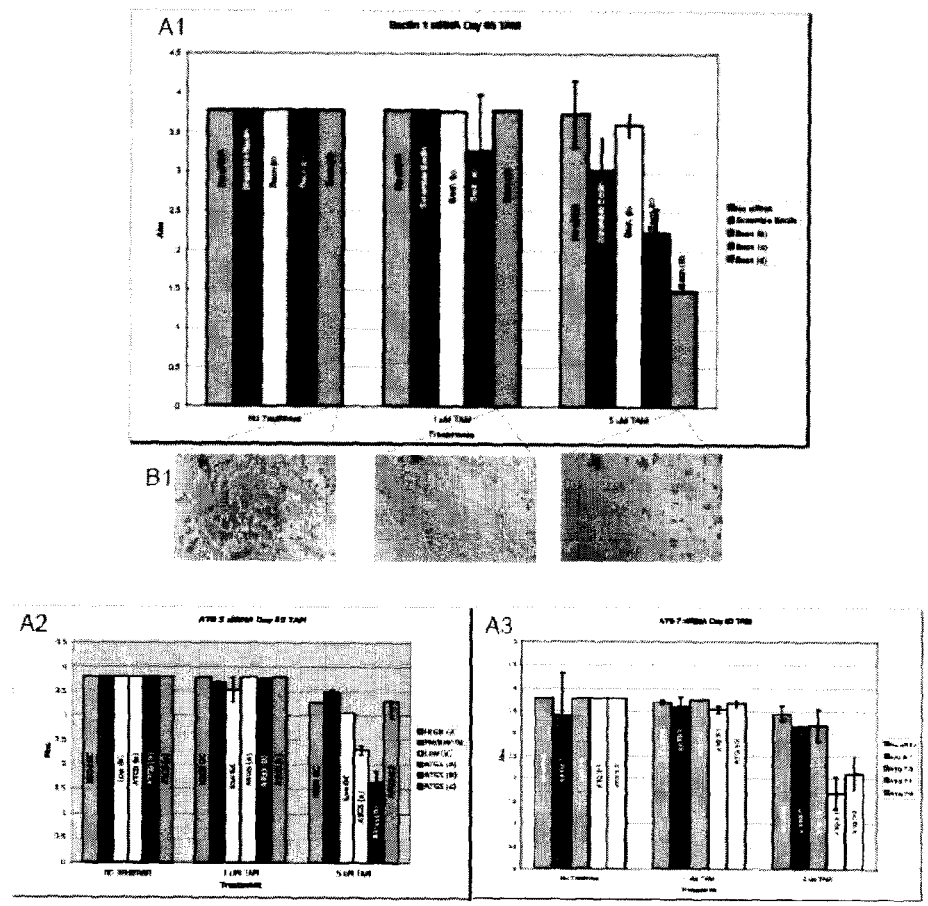
FIG. 14 is graphs and micrographs showing the effect of siRNA inhibition on tamoxifen treated MCF-7 cells by WST-1 assay.

FIG. 14. Effect of siRNA inhibition on Tamoxifen treated MCF-7 cells by WST-1 Assay. Panels A1, A2, and A3 are beclin 1, hAtg5 and hATG7 siRNA treated cells on Day 05 of Tamoxifen treatment. X-axis denotes untreated, 1×10-6 M and 5×10-6 M tamoxifen treated MCF-7 cells. Each siRNA panel contains the following: No siRNA (no treatment), negative control siRNA (s=scrambled siRNA; GC=GC content), and three siRNA molecules per gene). Results indicate that treatment with Atg-siRNA plus 5×10-6 M tamoxifen has an enhanced cell killing effect as seen in the corresponding cell images (B1).

Figure 15:
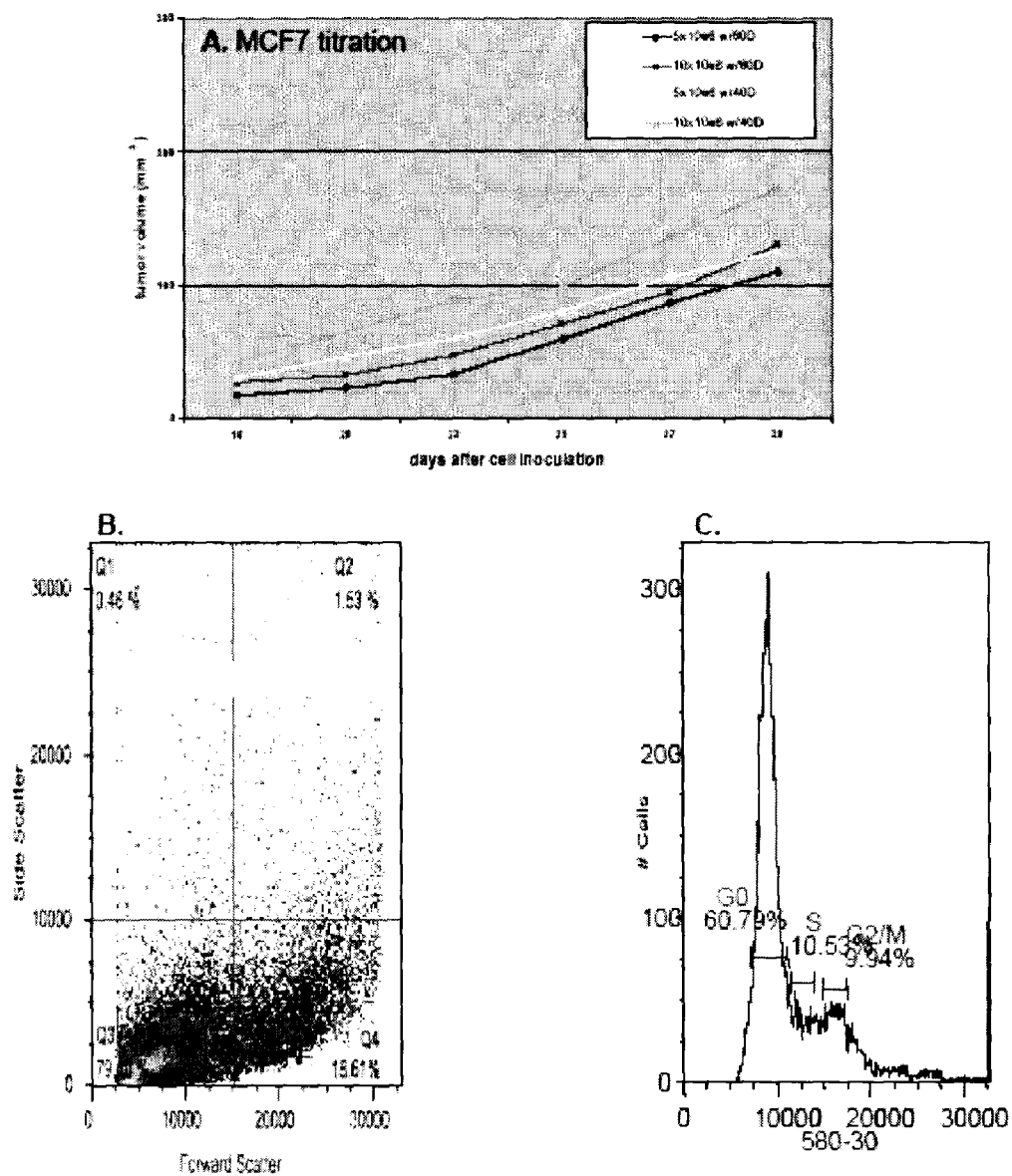
FIG. 15 is graphs showing growth of MCF-7 xenograft tumours in Rag2M mice.

FIG. 15. Growth and analysis of MCF7 xenograft tumours in Rag2M mice. A. Graph shows results of MCF7 tumour growth using different amounts of cells for inoculation and different concentrations of B-estradiol supplementation. Tumours were later harvested from mice, disaggregated, and human cells (i.e. MCF7) were separated by a flow sorter (B; in Q4), fixed and stained with propidium iodide for cell cycle analysis (C).

Example 4

Our previous findings indicate that autophagy knockdown combined with tamoxifen results in decreased cell viability and increased cell death relative to tamoxifen treatment alone. Methods of using in vivo embodiments in animals, for example to establish preferred approaches to treating selected cancers using an animal model, are described below.

Xenograft mouse model: Tumour studies in mice may be completed, for example in Rag2M mice. The Rag2M mice are knockout mice bred in the Animal Research Centre at BCCA. This line is deficient in the recombinase activating 2 gene (rag). Homozygous mice have a total inability to initiate V(D) J rearrangement, resulting in a failure to generate mature T or B lymphocytes. This results in the mice being ideally suitable for studies with human tumour lines. Mice may be inoculated with a quantity of cancer cells, such as $1\times10_7$ MCF7 cells subcutaneously into female Rag2M mice on Day 0. For MCF7 cell growth in vivo, mice require B-estradiol supplementation which will be initiated at day −1 (1.13 mg total dose B-estradiol pellet; 40 day release formulation, Innovative Research of America).

Tamoxifen treatment: At day 42, tamoxifen, or an alternative cancer therapy, may be administered, for example by implanting 21-day release 10 mg total dose tamoxifen (free base) pellets or corresponding placebo pellets for controls (dose as recommended by Innovative Research of America and our previous experience). The administration method may for example be chosen to avoid multiple s.c. injections that may cause added stress to the animals.

siRNA and delivery methods: Stealth™ RNAi technology from Invitrogen may for example be used. Stealth™ RNAi molecules are 25 bp RNA oligonucleotides with a proprietary chemical modification to ensure effective gene knockdown with higher specificity, greater stability and avoidance of stress response compared to traditional siRNA methods. Stealth RNAi has been proven effective at knockdown in cell culture and in vivo, and has been shown to be stable following incubation in mouse serum for up to 72 hours (16, 24). One duplexed siRNA may be selected for each Atg gene, for example for each of the beclin 1, hAtg7 and hAtg5 genes along with negative control siRNAs. A pilot study may first be conducted to optimize siRNA concentration, delivery, and treatment schedule in vivo. Both naked and liposomal formulation siRNA delivery methods may be tested, for example using intravenous injection in animals with established MCF7 tumours. Naked delivery (i.e. no carrier) has proven effective for anti-sense RNA and siRNA delivery (22, 23), and has the advantage that no other molecules are delivered. A second approach for siRNA delivery involves lipid encapsulation of the siRNA, designed to enhance siRNA half-life and thus enable use of lower does and reduced dosing frequency (24, 25). Stable Nucleic-Acid-Lipid Particle (SNALP) technology may for example be used, which consists of a lipid bilayer containing a mixture of cationic and fusogenic lipids (24), and has been proven effective in vivo (24). The delivery may be conducted using selected initial concentrations, such as 3 mg/kg siRNA (24, 25), equivalent to 60 ug per 20 g mouse. Serum stability of the siRNA may be determined at multiple timepoints as described (24). Knockdown of the corresponding gene and stress related genes may be determined by QRT-PCR of RNA isolated from harvested tumours. Autophagy protein levels may be measured by Western blot using available autophagy antibodies (Abnova, Abcam).

Figure 16:
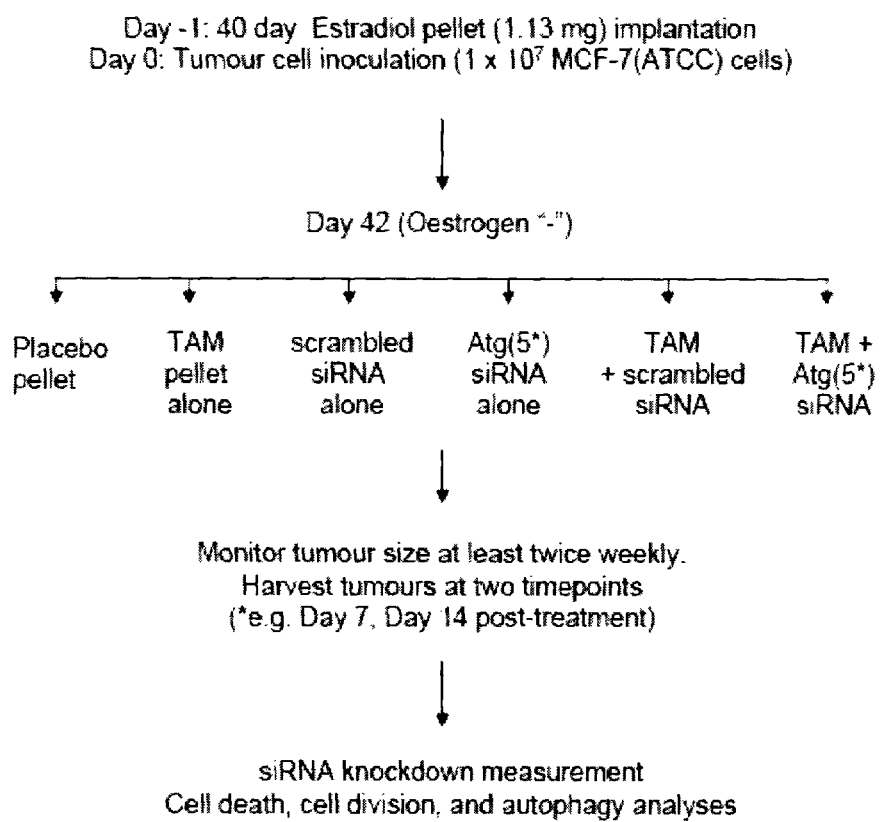
FIG. 16 is an overview of an animal treatment study.

Animal number and treatment study: Treatments may be assayed in representative groups of animals, such as 4 groups (siRNA negative control and siRNA treatment using 2 delivery methods) of 16 mice each (tumours+/−tamoxifen will be harvested at 2 timepoints). Tumour growth may be measured as described below. Measurement data may be subjected to the following statistical tests: Student's t test, ANOVA, Scheffe test, and Bonferonni. Results may be used to guide a treatment studies, which may for example include 6 groups (placebo pellet, tamoxifen pellet alone, siRNA negative control, siRNA treatment, tamoxifen plus siRNA control, tamoxifen plus siRNA treatment) consisting of an estimated 12 mice each (6 mice to undergo tumour harvest at 2 different timepoints) (FIG. 15). We estimate this number to be the minimum required based on expected losses of not more than 10%, and Power Analysis using the following parameters: an effect size of 2.0, a significance level of 0.05, a power of 90%, and a standard deviation of 1.5. It should be noted, however, that the standard deviation (amount of variance) is only an estimate and thus may be revised. A full treatment study (FIG. 16) may be conducted with siRNAs targeting two or more distinct human Atg genes Tumour Analyses: Tumour growth may be measured by digital caliper twice weekly once tumours are palpable and tumour size assessed by the following formula: $(L_2 \times W)/2$ where L=length and W=width, measured in mm. Mice may be terminated by $CO_2$ asphyxiation when tumour mass equals or exceeds 1 g, when tumours become ulcerated or if animals experience treatment related morbidity. At two timepoints, tumours may be harvested and divided into three parts for analyses as follows: Fraction A (approx ⅙ of tumour): to be placed in formalin and paraffin embedded between 24 and 72 hours post harvest. Unstained slides may be used to assess apoptosis (In Situ Cell Death Detection Kit, Roche), cell division (ki67 antibody), and autophagy (Beclin1 antibody). Fraction B (approx ⅜ of tumour) may have RNA and protein extracted for analysis of the autophagy marker LC3 and the target gene by QRTPCR and Western blot. Fraction C (approx ⅔ of tumour) may be disaggregated and human MCF7 cells separated for analysis of cell viability, cell cycle and autophagy by flow cytometry (e.g. FIG. 15).

The following example describes techniques for the use of two other ER-positive breast cancer cell lines and a normal control breast epithelial cell line to optimize and assay the effects of radiotherapy combined with siRNA autophagy inhibition on breast, ovarian, and colorectal cancer cell lines.

Cell lines: Two other breast cancer cell lines, BT-474 and MDA-MB-361, are available from American Type Culture Collection (ATCC). Like MCF7, these cell lines are estrogen receptor-positive and amenable to siRNA transfection. MCF7 cells may for example be included as a positive control and MCF-10A cells may be included to test for effects on normal breast epithelial cells. To explore alternative embodiments involving treatments with radiotherapy, one may for example use MCF7, HT-29 (colorectal adenocarcinoma), and SK-OV-3 (ovarian adenocarcinoma) cell lines. These cell lines are readily available, have the capacity to undergo autophagy induction (26, 27).

Tamoxifen and Irradiation treatments: Because the sensitivity of cell lines to treatments may differ, one may construct dose-response curves. For example, two concentrations of tamoxifen (equivalent to MCF7 treated with 1 uM and 5 uM) may be chosen for studies with siRNA. For radiotherapy studies, cells may be treated using a X-ray irradiator (Pantak, Seifert, X-RAD 320, Medical Bio-physics, BCCRC) for example with varying doses between 2 and 10 Gray, at a rate of 3.4 Gy/min as described previously (28). A "no treatment" (i.e. tamoxifen carrier ethanol alone or no irradiation) control may be included.

siRNA treatment and validation of gene knockdown: A si-RNA based strategy may be employed, specifically targeting a number of different autophagy genes (such as, beclin1, hAtg7, hAtg5). Three Stealth™ siRNA molecules (Invitrogen) per gene along with a siRNA negative control may for example be used. The siRNAs may for example be transfected using Lipofectamine 2000 (Invitrogen) and transfection efficiencies assayed by adding BLOCK-iT™ fluorescent oligos. Gene knockdown may be assessed by QRT-PCR for the targeted genes as well as for PKR and OSA-1 to elucidate any non-specific interferon mediated stress response. The RNAi assay may involve seeding $5 \times 10^3$ cells in 96 well format in the presence of OPTIMEM™ media (Invitrogen) with no antibiotics or phenol red. The following day, 5 pmole of siRNA complexed with Lipofectamine 2000™ in serum-free OPTI-MEM™ medium may be added. Following a 4 hr incubation, the cells may be treated with tamoxifen or irradiation as described above.

Cellular assays: Cells may be analyzed periodically, such as every 24 hours for 7 days. Cell metabolism may for example be assessed by employing the reagent, WST-1 (Roche). In addition, cell number, percent cell viability and percent cell death may be determined, for example using a live-dead cell assay and cell integrity assays (GE Healthcare) on an automated fluorescence microscopy platform (INCell Analyzer, Advanced Therapeutics, BCCRC). Cell death and apoptosis may be further assayed, for example using propidium iodide and Annexin-V (Molecular Probes). Cell cycle analysis may be performed using DRAQ5 (Alexis Biochemicals). Autophagy may be assessed initially using MDC (IN-Cell Analyzer) and then by LC3-based analyses (29). Clonogenic assays may be performed (30) to directly assay cell proliferation.

Statistical analyses: All cellular assays described above may be conducted in at least triplicate and the Student's t-test used to determine statistical significance. To define the degree of synergy of siRNA treatment combined with a cancer therapy such as tamoxifen or irradiation, one may use the approach developed by Chou and Talalay (31). Combinations resulting in more than an 80% cell effect (e.g. toxicity) may be considered synergistic in a clinically significant manner.

Many modifications to the exemplary embodiments described herein are possible. The invention, rather, is intended to encompass all such modification within its scope, as defined by the claims. Throughout the description, specific details are set forth in order to provide a more thorough understanding of the invention. However, alternative aspects of the invention may be practised without all of these particulars. In other instances, well known elements have not been shown or described in detail to avoid unnecessarily obscuring the invention. Accordingly, the specification and drawings are to be regarded in an illustrative, rather than a restrictive sense.

As used herein, the singular article "a" or "an" is intended to mean "one or more" unless specifically indicated otherwise.

All documents referred to herein are fully incorporated by reference.

Although various embodiments of the invention are disclosed herein, many adaptations and modifications may be made within the scope of the invention in accordance with the common general knowledge of those skilled in this art. Such modifications include the substitution of known equivalents for any aspect of the invention in order to achieve the same result in substantially the same way. All technical and scientific terms used herein have the same meaning as commonly understood by one of ordinary skill in the art of this invention, unless defined otherwise.

REFERENCES

1. Canadian Cancer Statistics, 2004. (www.cancer.ca)
2. Levine B, Klionsky D J: Development by self-digestion: molecular mechanisms and biological functions of autophagy. Dev Cell. 2004, 6(4): 463-77.
3. Shintani T, Klionsky D J: Autophagy in health and disease: a double-edged sword. Science 2004, 306:990-995.
4. Klionsky D J, and Emr S D: Autophagy as a regulated pathway of cellular degradation. Science 2000, 290: 1717-1721.
5. Sledz, C. A., Holko, M., de Veer, M. J., Silverman, R. H., and Williams, B. R. G. (2003). Activation of the Interferon System by Short-Interfering RNAs. Nature Cell Biol. 5, 834-839.12. Yue Z, Jin S, Yang C, Levine A J, Heintz N: Proc Natl Acad Sci USA. 2003, 100(25): 15077-82.2003.
6. Bursch W, Ellinger A, Kienzl H. Torok L, Pandey S, Sikorska M, Walker R, Hermann R S: Active cell death induced by the anti-estrogens tamoxifen and ICI 164 384 in human mammary carcinoma cells (MCF-7) in culture: the role of autophagy. Carcinogenesis 1996, 17: 1595-1607.
7. Bilir A, Altinoz M A, Erkan M, Ozmen V, Aydiner A: Autophagy and nuclear changes in FM3A breast tumor cells after epirubicin, medroxyprogesterone and tamoxifen treatment in vitro. Pathobiology. 2001, 69(3): 120-6
8. Paglin S, Hollister T, Delohery T, Hackett N, McMahill M, Sphicas E, Domingo D, Yahalom J: A novel response of cancer cells to radiation involves autophagy and formation of acidic vesicles. Cancer Res 2001, 61: 439-444.
9. McManus M T, Sharp P A: Gene silencing in mammals by small interfering RNAs. Nat Rev Genet. 2002, 3(10): 737-47.
10. Bursch W, Hochegger K, Torok L, Marian B, Ellinger A, Hermann R S: Autophagic and apoptotic types of programmed cell death exhibit different fates of cytoskeletal filaments. J Cell Sci. 2000, 113 (Pt 7): 1189-98
11. Boya P, Gonzalez-Polo R, Casares N, Perfettini J, Dessen P, Larochette N, Metivier D, Meley D, Souquere S, Yoshimori T, Pierron G, Codogno P, Kroemer G: Inhibition of Macroautophagy Triggers Apoptosis. Mol. Cell. Biol. 2005, 25: 1025-1040.
12. Sledz C A, Holko M, de Veer M J, Silverman R H, Williams B R: Activation of the interferon system by short-interfering RNAs. Nat Cell Biol. 2003, 5(9): 834-9.
13. Mizushima N: Methods for monitoring autophagy. Int J Biochem Cell Biol. 2004, 36(12): 2491-502
14. Dragowska W H, Warburton C, Yapp D T, Minchinton A I, Hu Y, Waterhouse D N, Gelmon K, Skov K, Woo J, Masin D, Huxham L A, Kyle A H, Bally M B: HER-2/neu overexpression increases the viable hypoxic cell population within solid tumors without causing changes in tumor vascularization. Mol Cancer Res. 2004 November; 2(11):606-19.
15. Dawn N. Waterhouse, Tetyana Denyssevych, Norma Hudon, Stephen Chia, Karen A. Gelmon, and Marcel B. Bally: Trastuzumab and Liposomal Doxorubicin in the Treatment of MCF-7 Xenograft Tumor-Bearing Mice: Combination does not affect drug serum levels.
16. Submitted, Pharmaceutical Research.
17. Brummelkamp T R, Bernards R, Agami R: A system for stable expression of short interfering RNAs in mammalian cells. Science. 2002 Apr. 19; 296(5567):550-3.
18. Bursch W, Ellinger A, Kienzl H, Torok L, Pandey S, Sikorska M, Walker R, Hermann R S: Active cell death induced by the anti-estrogens tamoxifen and ICI 164 384 in human mammary carcinoma cells (MCF-7) in culture: the role of autophagy. Carcinogenesis. 1996 August; 17(8): 1595-607.
19. Minakuchi Y, Takeshita F, Kosaka N, Sasaki H, Yamamoto Y, Kouno M, Honma K, Nagahara S, Hanai K, Sano A, Kato T, Terada M, Ochiya T: Atelocollagen-mediated synthetic small interfering RNA delivery for effective gene silencing in vitro and in vivo. Nucleic Acids Res. 2004 Jul. 22; 32(13):e109.
20. Lee J H, Cho E S, Kim M Y, Seo Y W, Kho D H, Chung I J, Kook H, Kim N S, Ahn K Y, Kim K K: Suppression of progression and metastasis of established colon tumors in mice by intravenous delivery of short interfering RNA targeting KITENIN, a metastasis-enhancing protein. Cancer Res. 2005 Oct. 1; 65(19):8993-9003.
21. Yu L, Alva A, Su H, Dutt P, Freundt E, Welsh S, Baehrecke E H, Lenardo M J: Regulation of an ATG7-beclin 1 program of autophagic cell death by caspase-8. Science 2004, 304(5676): 1500-2.
22. Bonetta L. RNAi: Silencing never sounded better. Nature Methods 2004, 1(1):79-86.
23. Pushparaj P N, Melendez A J. Short interfering RNA (siRNA) as a novel therapeutic. Clin Exp Pharmacol Physiol 2006; 33(5-6):504-10.
24. Morrissey D V, Lockridge J A, Shaw L, Blanchard K, Jensen K, Breen W, et al. Potent and persistent in vivo anti-HBV activity of chemically modified siRNAs. Nat Biotechnol 2005; 23(8):1002-7.
25. Santel A, Aleku M, Keil O, Endruschat J, Esche V, Durieux B, et al. RNA interference in the mouse vascular endothelium by systemic administration of siRNA-lipoplexes for cancer therapy. Gene Ther 2006.
26. Pattingre S, Tassa A, Qu X, Garuti R, Liang X H, Mizushima N, et al. Bcl-2 antiapoptotic proteins inhibit Beclin 1-dependent autophagy. Cell 2005; 122(6):927-39.
27. Opipari A W, Jr., Tan L, Boitano A E, Sorenson D R, Aurora A, Liu J R. Resveratrol induced autophagocytosis in ovarian cancer cells. Cancer Res 2004; 64(2):696-703.
28. Ito H, Daido S, Kanzawa T, Kondo S, Kondo Y. Radiation-induced autophagy is associated with LC3 and its inhibition sensitizes malignant glioma cells. Int J Oncol 2005; 26(5):1401-10.
29. Mizushima N: Methods for monitoring autophagy. Int J Biochem Cell Biol. 2004, 36(12): 2491-502
30. Breast Cancer Therapeutics: 2006 How Innovation is Shaping Future Therapies
31. Chou T C, Talalay P. Quantitative analysis of dose-effect relationships: the combined effects of multiple drugs or enzyme inhibitors. Adv Enzyme Regul 1984; 22:27-55.

What is claimed is:

1. A method of increasing a cellular response to a cancer therapy comprising inhibiting expression of a Beclin 1 (Atg6) gene in a breast cancer cell in a human patient currently undergoing the cancer therapy, wherein the cancer therapy comprises administration of an effective amount of tamoxifen or a taxane, and said inhibiting comprises contacting the cell with an siRNA encapsulated in a liposome in an amount effective to inhibit expression of the Beclin 1 gene.

2. A method of treating a breast cancer in a human patient in need thereof comprising administering to the patient an siRNA encapsulated in a liposome in an amount effective to inhibit expression of a Beclin 1 (Atg6) gene, in combination with a cancer therapy, wherein the cancer therapy comprises administration of an effective amount of tamoxifen or a taxane.

3. The method of claim 1, wherein said siRNA comprises a sequence as set forth in any one of SEQ ID NO.:1, 2, 3, 4, 5, 13, 16, 24, 25 or 26.

4. The method of claim 3 wherein said siRNA comprises a sequence consisting essentially of the sequence as set forth in any one of SEQ ID NO.: 1, 2, 3, 4, 5, 13, 16, 24, 25, or 26.

5. The method of claim 4 wherein said siRNA comprises a sequence consisting of the sequence as set forth in any one of SEQ ID NO.: 1, 2, 3, 4, 5, 13, 16, 24, 25, or 26.

6. The method of claim 3 wherein the siRNA further comprises a chemical modification.

7. The method of claim 1 wherein the cancer therapy further comprises endocrine therapy, chemotherapy or radiation therapy.

* * * * *

SEQUENCE LISTING

```
<160> NUMBER OF SEQ ID NOS: 28

<210> SEQ ID NO 1
<211> LENGTH: 25
<212> TYPE: RNA
```

```
<213> ORGANISM: Artificial Sequence
<220> FEATURE:
<223> OTHER INFORMATION: synthetic siRNA oligonucleotide

<400> SEQUENCE: 1
gcuguuugga gaucuuagag caaau                                              25

<210> SEQ ID NO 2
<211> LENGTH: 25
<212> TYPE: RNA
<213> ORGANISM: Artificial Sequence
<220> FEATURE:
<223> OTHER INFORMATION: synthetic siRNA oligonucleotide

<400> SEQUENCE: 2
ggaugaugag cugaagagug uugaa                                              25

<210> SEQ ID NO 3
<211> LENGTH: 25
<212> TYPE: RNA
<213> ORGANISM: Artificial Sequence
<220> FEATURE:
<223> OTHER INFORMATION: synthetic siRNA oligonucleotide

<400> SEQUENCE: 3
uaucugugca uuccucacag agugg                                              25

<210> SEQ ID NO 4
<211> LENGTH: 25
<212> TYPE: RNA
<213> ORGANISM: Artificial Sequence
<220> FEATURE:
<223> OTHER INFORMATION: synthetic siRNA oligonucleotide

<400> SEQUENCE: 4
agcugcuguc guuuaaauuc acugu                                              25

<210> SEQ ID NO 5
<211> LENGTH: 25
<212> TYPE: RNA
<213> ORGANISM: Artificial Sequence
<220> FEATURE:
<223> OTHER INFORMATION: synthetic siRNA oligonucleotide

<400> SEQUENCE: 5
uucaacacuc uucagcucau caucc                                              25

<210> SEQ ID NO 6
<211> LENGTH: 25
<212> TYPE: RNA
<213> ORGANISM: Artificial Sequence
<220> FEATURE:
<223> OTHER INFORMATION: synthetic siRNA oligonucleotide

<400> SEQUENCE: 6
gcuggaugaa gcucccaagg acauu                                              25

<210> SEQ ID NO 7
<211> LENGTH: 25
<212> TYPE: RNA
<213> ORGANISM: Artificial Sequence
<220> FEATURE:
<223> OTHER INFORMATION: synthetic siRNA oligonucleotide

<400> SEQUENCE: 7
ccaaggaugg ugaaccucag ugaau                                              25
```

```
<210> SEQ ID NO 8
<211> LENGTH: 25
<212> TYPE: RNA
<213> ORGANISM: Artificial Sequence
<220> FEATURE:
<223> OTHER INFORMATION: synthetic siRNA oligonucleotide

<400> SEQUENCE: 8
aaaccuuuga uccaaaccca cuggc                                    25

<210> SEQ ID NO 9
<211> LENGTH: 25
<212> TYPE: RNA
<213> ORGANISM: Artificial Sequence
<220> FEATURE:
<223> OTHER INFORMATION: synthetic siRNA oligonucleotide

<400> SEQUENCE: 9
gaucacaagc aacucuggau gggau                                    25

<210> SEQ ID NO 10
<211> LENGTH: 25
<212> TYPE: RNA
<213> ORGANISM: Artificial Sequence
<220> FEATURE:
<223> OTHER INFORMATION: synthetic siRNA oligonucleotide

<400> SEQUENCE: 10
auuccaugag uuuccgauug auggc                                    25

<210> SEQ ID NO 11
<211> LENGTH: 25
<212> TYPE: RNA
<213> ORGANISM: Artificial Sequence
<220> FEATURE:
<223> OTHER INFORMATION: synthetic siRNA oligonucleotide

<400> SEQUENCE: 11
aaacaaguug gaauucgucc aaacc                                    25

<210> SEQ ID NO 12
<211> LENGTH: 25
<212> TYPE: RNA
<213> ORGANISM: Artificial Sequence
<220> FEATURE:
<223> OTHER INFORMATION: synthetic siRNA oligonucleotide

<400> SEQUENCE: 12
aucccaucca gaguugcuug ugauc                                    25

<210> SEQ ID NO 13
<211> LENGTH: 25
<212> TYPE: RNA
<213> ORGANISM: Artificial Sequence
<220> FEATURE:
<223> OTHER INFORMATION: synthetic siRNA oligonucleotide

<400> SEQUENCE: 13
auuugcucua agaucuccaa acagc                                    25

<210> SEQ ID NO 14
<211> LENGTH: 25
<212> TYPE: RNA
<213> ORGANISM: Artificial Sequence
<220> FEATURE:
<223> OTHER INFORMATION: synthetic siRNA oligonucleotide
```

```
<400> SEQUENCE: 14
gcuuugggau aucauagcga ugaau                                              25

<210> SEQ ID NO 15
<211> LENGTH: 25
<212> TYPE: RNA
<213> ORGANISM: Artificial Sequence
<220> FEATURE:
<223> OTHER INFORMATION: synthetic siRNA oligonucleotide

<400> SEQUENCE: 15
auucaucgcu augauaccc aaagc                                               25

<210> SEQ ID NO 16
<211> LENGTH: 25
<212> TYPE: RNA
<213> ORGANISM: Artificial Sequence
<220> FEATURE:
<223> OTHER INFORMATION: synthetic siRNA oligonucleotide

<400> SEQUENCE: 16
uucaacacuc uucagcucau caucc                                              25

<210> SEQ ID NO 17
<211> LENGTH: 25
<212> TYPE: RNA
<213> ORGANISM: Artificial Sequence
<220> FEATURE:
<223> OTHER INFORMATION: synthetic siRNA oligonucleotide

<400> SEQUENCE: 17
ggaaguaguc gagaaugugu gugaa                                              25

<210> SEQ ID NO 18
<211> LENGTH: 25
<212> TYPE: RNA
<213> ORGANISM: Artificial Sequence
<220> FEATURE:
<223> OTHER INFORMATION: synthetic siRNA oligonucleotide

<400> SEQUENCE: 18
aauguccuug ggagcuucau ccagc                                              25

<210> SEQ ID NO 19
<211> LENGTH: 25
<212> TYPE: RNA
<213> ORGANISM: Artificial Sequence
<220> FEATURE:
<223> OTHER INFORMATION: synthetic siRNA oligonucleotide

<400> SEQUENCE: 19
auucacugag guucaccauc cuugg                                              25

<210> SEQ ID NO 20
<211> LENGTH: 25
<212> TYPE: RNA
<213> ORGANISM: Artificial Sequence
<220> FEATURE:
<223> OTHER INFORMATION: synthetic siRNA oligonucleotide

<400> SEQUENCE: 20
aaauccuuuc cuagaaacac ccggc                                              25

<210> SEQ ID NO 21
<211> LENGTH: 25
<212> TYPE: RNA
```

```
<213> ORGANISM: Artificial Sequence
<220> FEATURE:
<223> OTHER INFORMATION: synthetic siRNA oligonucleotide

<400> SEQUENCE: 21
gccggguguu ucuaggaaag gauuu                                              25

<210> SEQ ID NO 22
<211> LENGTH: 25
<212> TYPE: RNA
<213> ORGANISM: Artificial Sequence
<220> FEATURE:
<223> OTHER INFORMATION: synthetic siRNA oligonucleotide

<400> SEQUENCE: 22
gccaucaauc ggaaacucau ggaau                                              25

<210> SEQ ID NO 23
<211> LENGTH: 25
<212> TYPE: RNA
<213> ORGANISM: Artificial Sequence
<220> FEATURE:
<223> OTHER INFORMATION: synthetic siRNA oligonucleotide

<400> SEQUENCE: 23
gguuuggacg aauccaacu uguuu                                               25

<210> SEQ ID NO 24
<211> LENGTH: 25
<212> TYPE: RNA
<213> ORGANISM: Artificial Sequence
<220> FEATURE:
<223> OTHER INFORMATION: synthetic siRNA oligonucleotide

<400> SEQUENCE: 24
ccacucugug aggaaugcac agaua                                              25

<210> SEQ ID NO 25
<211> LENGTH: 25
<212> TYPE: RNA
<213> ORGANISM: Artificial Sequence
<220> FEATURE:
<223> OTHER INFORMATION: synthetic siRNA oligonucleotide

<400> SEQUENCE: 25
acagugaauu uaaacgacag cagcu                                              25

<210> SEQ ID NO 26
<211> LENGTH: 25
<212> TYPE: RNA
<213> ORGANISM: Artificial Sequence
<220> FEATURE:
<223> OTHER INFORMATION: synthetic siRNA oligonucleotide

<400> SEQUENCE: 26
ggaugaugag cugaagagug uugaa                                              25

<210> SEQ ID NO 27
<211> LENGTH: 25
<212> TYPE: RNA
<213> ORGANISM: Artificial Sequence
<220> FEATURE:
<223> OTHER INFORMATION: synthetic siRNA oligonucleotide

<400> SEQUENCE: 27
gccggguguu ucuaggaaag gauuu                                              25
```

```
<210> SEQ ID NO 28
<211> LENGTH: 25
<212> TYPE: RNA
<213> ORGANISM: Artificial Sequence
<220> FEATURE:
<223> OTHER INFORMATION: synthetic siRNA oligonucleotide

<400> SEQUENCE: 28
aaauccuuuc cuagaaacac ccggc                                     25
```